US007238360B2

(12) United States Patent
Shirwan

(10) Patent No.: US 7,238,360 B2
(45) Date of Patent: Jul. 3, 2007

(54) ALTERATION OF CELL MEMBRANE WITH B7

(75) Inventor: Haval Shirwan, Louisville, KY (US)

(73) Assignee: Unversity of Louisville Research Foundation, Inc., Louisville, KY (US)

(*) Notice: Subject to any disclaimer, the term of this patent is extended or adjusted under 35 U.S.C. 154(b) by 195 days.

(21) Appl. No.: 10/312,245

(22) PCT Filed: Jul. 2, 2001

(86) PCT No.: PCT/US01/20946

§ 371 (c)(1),
(2), (4) Date: May 16, 2003

(87) PCT Pub. No.: WO02/02751

PCT Pub. Date: Jan. 10, 2002

(65) Prior Publication Data

US 2003/0219419 A1    Nov. 27, 2003

Related U.S. Application Data

(60) Provisional application No. 60/215,580, filed on Jun. 30, 2000.

(51) Int. Cl.
*A61K 39/385* (2006.01)
*A61K 38/17* (2006.01)
*C07K 14/705* (2006.01)
*C07H 21/04* (2006.01)
*C12N 5/10* (2006.01)

(52) U.S. Cl. ............... 424/277.1; 435/354; 435/355; 435/366; 435/372; 435/375; 514/12; 530/350; 530/816; 536/23.4

(58) Field of Classification Search ............ 424/85.1; 435/69.7, 252.3, 325; 514/12; 530/350, 530/810, 825
See application file for complete search history.

(56) References Cited

U.S. PATENT DOCUMENTS

| | | | | |
|---|---|---|---|---|
| 6,042,826 | A | 11/1997 | Caligiuri et al. | 424/130.1 |
| 5,763,223 | A | 6/1998 | Wiley et al. | 435/69.5 |
| 5,858,776 | A | 1/1999 | Ostrand-Rosenberg et al. | |
| 6,004,942 | A | 12/1999 | Firestein et al. | 514/44 |
| 6,071,716 | A | 6/2000 | Freeman et al. | |
| 6,130,316 | A | 10/2000 | Freeman et al. | |
| 6,149,905 | A | 11/2000 | Ostrand-Rosenberg et al. | |
| 6,218,510 | B1 | 4/2001 | Sharpe et al. | |
| 6,294,660 | B1 | 9/2001 | Sharpe et al. | |
| 6,319,709 | B1 | 11/2001 | Ostrand-Rosenberg et al. | |
| 6,608,180 | B2 | 8/2003 | Sharpe et al. | |
| 6,653,444 | B1 | 11/2003 | Freeman et al. | |

FOREIGN PATENT DOCUMENTS

| | | |
|---|---|---|
| WO | WO-97/18307 | 5/1997 |
| WO | WO-99/17801 | 4/1999 |
| WO | WO 9917801 A2 * | 4/1999 |
| WO | WO-01/52664 | 7/2001 |

OTHER PUBLICATIONS

Berzofsky JA, Terabe M, Oh S, Belyakov IM, Ahlers JD, Janik JE, Morris JC. 2004. Progress on new vaccine strategies for the immunotherapy and prevention of cancer. Journal of Clinical Investigation, 113(11): 1515-1525.*
Singh NP, Yolcu ES, Taylor DD, Gercel-Taylor C, Metzinger DS, Dreisbach SK, Shirwan H. 2003. A novel approach to cancer immunotherapy: tumor cells decorated with CD80 generate effective antitumor immunity. Cancer Research 63, 4067-4073.*
Yolcu ES, Askenasy N, Singh NP, Cherradi SE, Shirwan H. 2002. Cell membrane modification for rapid display of proteins as a novel means of immunomodulation: FasL-decorated cells prevent islet graft rejection. Immunity, 17: 795-808.*
Brunschwig EB, Levine E, Trefzer U, Tykocinski ML. 1995. Glycosylphosphatidylinositol-modified murine B7-1 and B7-2 retain costimulator function.Journal of Immunology. 155:5498-5505.*
Sano T, Pandori MW, Chen X, Smith CL, Cantor CR. Nov. 24, 1995. Recombinant core streptavidins. Journal of Biological Chemistry. 270(47):28204-28209.*
Le et al, 1994. Enzyme Microb. Technol. 16: 496-500.*
Green et al, 1990. Methods in Enzymology. 184: 51-67.*
Pettit et al. 1998. Trends Biotechnol. 16: 343-349.*
Pierce Instructions for EZ-LINK Sulfo-NHS-LC-Biotin Instructions, 1998, 4 pages.*
Sigma No. B2463 Product Information, Dec. 19, 1996, 2 pages.*
Phillips, A., J Pharm Pharmacology 53: 1169-1174, 2001.*
Chen, A., et al., "Hierarchical Costimulator Thresholds for Distinct Immune Responses: Application of a Novel Two-Step Fc Fustion Protein Transfer Method," *The Journal of Immunology*, 164, (2000), 705-711.
Darling, D., et al., "In Vitro Immune Modulation by Antibodies Coupled to Tumour Cells," *Gene Therapy*, 4, (1997), 1350-1360.
Sano, Takeshi, et al., "A streptavidin-metallothionein chimera that allows specific labeling of biological materials with many different heavy metal ions," *Proc. Nat'l. Acad. Sci. USA*, vol. 89, (Mar. 1992), 1534-1538.
Yolcu et al., 2002, Cell Membrane Modification for Rapid Display of Proteins as a Novel Means of Immunomodulation: FasL Decorated Cells Prevent Islet Graft Rejection, *Immunity*, 17:795-808.

(Continued)

*Primary Examiner*—Elizabeth Kemmeref
*Assistant Examiner*—Zachary C. Howard
(74) *Attorney, Agent, or Firm*—Foley & Lardner LLP

(57) ABSTRACT

Methods and compositions are provided for the persistent modification of cell membranes with exogenous proteins so as to alter the function of the cell to achieve effects similar to those of gene therapy, without the introduction of exogenous DNA. DNA sequences, the proteins and polypeptides embodying these sequences are disclosed for modulating the immune system. The modulations include down-regulation, up-regulation and apoptosis.

23 Claims, 9 Drawing Sheets

OTHER PUBLICATIONS

Askenasy et al., 2003, Display of Fas Ligand Protein on Cardiac Vasculature as a Novel Means of Regulating Allograft Rejection, *Circulation*, 107:r41-r47.

Chen et al., "Hierarchical Costimulator Thresholds for Distinct Immune Responses: Application of a Novel Two-Step Fc Fusion Protein Transfer Method," *The Journal of Immunology*, 164:705-711 (2000).

* cited by examiner

SEQUENCE LISTING

<160> NUMBER OF SEQ ID NOS: 7

<210> SEQ ID NO 1
<211> LENGTH: 1247
<212> TYPE: DNA
<213> ORGANISM: Artificial Sequence
<220> FEATURE:
<223> OTHER INFORMATION: SA-FasL

<400> SEQUENCE: 1

```
cgaacgaaag acccgtgtgt aaagccgcgt ttccaaaatg tataaaaccg agagcatctg      60
gccaatgtgc atcagttgtg gtcagcagca aaatcaagtg aatcatctca gtgcaactaa     120
aggggggatc cgatctcaat atgaagttat gcatattact ggccgtcgtg gccttttgttg   180 gcctctcgct cgggagatct catcatcacc atcaccatat caccggcacc tggtacaacc    240
agctcggctc gaccttcatc gtgaccgcgg gcgccgacgg cgccctgacc ggaacctacg    300
agtcggccgt cggcaacgcc gagagccgct acgtcctgac cggtcgttac gacagcgccc    360
cggccaccga cggcagcggc accgccctcg gttggacggt ggcctggaag aataactacc    420
gcaacgccca ctccgcgacc acgtggagcg gccagtacgt cggcggcgcc gaggcgagga    480
tcaacaccca gtggctgctg acctccggca ccaccgaggc caacgcctgg aagtccacgc    540
tggtcggcca cgacaccttc accaaggtga agccgtccgc cgcctcaagc cgaattcctg    600
```

| | |
|---|---|
| aaaccaaaaa gccaaggagt gtggcccact taacagggaa ccccegctca aggtccatcc | 660 |
| ctctggaatg ggaagacaca tatgaactg ctttgatctc tggagtgaag tataagaaag | 720 |
| gcggccttgt gatcaatgag gctgggttgt acttcgtata ttccaaagta tacttccggg | 780 |
| gtcagtcttg caacagccag cccctaagcc acaaggtcta tgaggaac tttaagtatc | 840 |
| ctggggatct ggtgctaatg gaggagaaga agttgaatta ctgcactact ggccagatat | 900 |
| gggcccacag cagctaccta ggggcagtat ttaatcttac cgttgctgac catttatatg | 960 |
| tcaacatatc tcaactctct ctgatcaatt ttgaggaatc taagacctt tttggcttat | 1020 |
| ataagcttta aggaaaaag cattttagaa tgatctatta ttctttatca tggatgccag | 1080 |
| gaatattgtc ttcaatgaga gtcttcttaa gaccaattga gccacaaaga ccacaaggtc | 1140 |
| caacaggtca gctaccctga attctgcaga tatccagcac agtggcggcc gctcgagtct | 1200 |
| agagggccct tcgaaggtaa gcctatccct aaccctctcc tcggtct | 1247 |

<210> SEQ ID NO 2
<211> LENGTH: 1542
<212> TYPE: DNA
<213> ORGANISM: Artificial Sequence
<220> FEATURE:
<223> OTHER INFORMATION: B7.1-SA

<400> SEQUENCE: 2

| | |
|---|---|
| cgaacgaaag acccgtgtgt aaagccgcgt ttccaaaatg tataaaaccg agagcatctg | 60 |
| gccaatgtgc atcagttgtg gtcagcagca aaatcaagtg aatcatctca gtgcaactaa | 120 |
| agggggatc cgatctcaat atgaagttat gcatattact ggccgtcgtg gcctttgttg | 180 |
| gcctctcgct cggggtaag agatctatcc acgtgaccaa ggaagtgaaa gaagtggcaa | 240 |
| cgctgtcctg tggtcacaat gtttctgttg aagagctggc acaaactcgc atctactggc | 300 |
| aaaaggagaa gaaatggtg ctgactatga tgtctgggga catgaatata tggcccgagt | 360 |
| acaagaaccg gaccatcttt gatatcacta ataacctctc cattgtgatc ctggctctgc | 420 |
| gcccatctga cgagggcaca tacgagtgtg ttgttctgaa gtatgaaaaa gacgctttca | 480 |
| agcgggaaca cctggctgaa gtgacgttat cagtcaaagc tgacttccct acacctagta | 540 |
| tatctgactt tgaaattcca acttctaata ttagaaggat aatttgctca acctctggag | 600 |
| gttttccaga gcctcacctc tcctggttgg aaaatggaga agaattaaat gccatcaaca | 660 |
| caacagtttc ccaagatcct gaaactgagc tctatgctgt tagcagcaaa ctggatttca | 720 |
| atatgacaac caaccacagc ttcatgtgtc tcatcaagta tggacattta agagtgaatc | 780 |
| agaccttcaa ctggaataca accaagcaag agagatctag atctcatcat caccatcacc | 840 |
| atatcaccgg cacctggtac aaccagctcg gctcgacctt catcgtgacc gcgggcgccg | 900 |
| acggcgccct gaccggaacc tacgagtcgg ccgtcggcaa cgccgagagc cgctacgtcc | 960 |
| tgaccggtcg ttacgacagc gccccggcca ccgacgcag cggcaccgcc tcggttgga | 1020 |
| cggtggcctg gaagaataac taccgcaacg cccactccgc gaccacgtgg agcggccagt | 1080 |
| acgtcggcgg cgccgaggcg aggatcaaca cccagtgget gctgacctcc ggcaccaccg | 1140 |
| aggccaacgc ctggaagtcc acgctggtcg gccacgacac cttcaccaag gtgaagccgt | 1200 |
| ccgccgcctc gaattctgc agatatccag cacagtggcg gccgctcgag tctagagggc | 1260 |
| ccttcgaagg taagcctatc cctaaccctc tcctcggtct cgattctacg cgtaccggtc | 1320 |
| atcatcacca tcaccattga gtttaaaccc gctgatcagc ctcgactgtg ccttctaagg | 1380 |
| cctgagctcg ctgatcagcc tcgatcgagg atccagacat gataagatac attgatgagt | 1440 |

```
ttggacaaac cacaactaga atgcagtgaa aaaaatgctt tatttgtgaa atttgtgatg    1500
ctattgcttt atttgtaacc attataagct gcaataaaca ag                      1542

<210> SEQ ID NO 3
<211> LENGTH: 1266
<212> TYPE: DNA
<213> ORGANISM: Artificial Sequence
<220> FEATURE:
<223> OTHER INFORMATION: TGF-B-SA

<400> SEQUENCE: 3
cgaacgaaag acccgtgtgt aaagccgcgt ttccaaaatg tataaaaccg agagcatctg    60
gccaatgtgc atcagttgtg gtcagcagca aaatcaagtg aatcatctca gtgcaactaa   120
aggggggatc cgatctcaat atgaagttat gcatattact ggccgtcgtg gcctttgttg   180
gcctctcgct cggggtaag agatctgccc tggacaccaa ctattgcttc agctccacgg    240
agaagaactg ctgcgtgcgg cagctgtaca ttgacttccg caaggacctc ggctggaagt   300
ggatccacga gcccaagggc taccatgcca acttctgcct cgggccctgc ccctacattt   360
ggagcctgga cacgcagtac agcaaggtcc tggccctgta caaccagcat aacccgggcg   420
cctcggcggc gccgtgctgc gtgccgcagg cgctggagcc gctgcccatc gtgtactacg   480
tgggccgcaa gcccaaggtg gagcagctgt ccaacatgat cgtgcgctcc tgcaagtgca   540
gcagatctca tcatcaccat caccatatca ccggcacctg gtacaaccag ctcggctcga   600
ccttcatcgt gaccgcgggc gccgacggcg ccctgaccgg aacctacgag tcggccgtcg   660
gcaacgccga gagccgctac gtcctgaccg gtcgttacga cagcgccccg gccaccgacg   720
gcagcggcac cgccctcggt tggacggtgg cctggaagaa taactaccgc aacgcccact   780
ccgcgaccac gtggagcggc cagtacgtcg gcggcgccga ggcgaggatc aacacccagt   840
ggctgctgac ctccggcacc accgaggcca acgcctggaa gtccacgctg gtcggccacg   900
acaccttcac caaggtgaag ccgtccgccg cctccgaatt ctgcagatat ccagcacagt   960
ggcggccgct cgagtctaga gggcccttcg aaggtaagcc tatccctaac cctctcctcg   1020
gtctcgattc tacgcgtacc ggtcatcatc accatcacca ttgagtttaa acccgctgat   1080
cagcctcgac tgtgccttct aaggcctgag ctcgctgatc agcctcgatc gaggatccag   1140
acatgataag atacattgat gagtttggac aaaccacaac tagaatgcag tgaaaaaaat   1200 gcttttatttg tgaaatttgt gatgctattg ctttatttgt aaccattata agctgcaata   1260
aacaag                                                              1266

<210> SEQ ID NO 4
<211> LENGTH: 1329
<212> TYPE: DNA
<213> ORGANISM: Artificial Sequence
<220> FEATURE:
<223> OTHER INFORMATION: IL-2-SA

<400> SEQUENCE: 4
cgaacgaaag acccgtgtgt aaagccgcgt ttccaaaatg tataaaaccg agagcatctg    60
gccaatgtgc atcagttgtg gtcagcagca aaatcaagtg aatcatctca gtgcaactaa   120
aggggggatc cgatctcaat atgaagttat gcatattact ggccgtcgtg gcctttgttg   180
gcctctcgct cgggagatct ccagcaccta cttcaagttc tacaaagaaa acacagctac   240
aactggagca tttactgctg gatttacaga tgattttgaa tggaattaat aattacaaga   300
```

```
atcccaaact caccaggatg ctcacattta agttttacat gcccaagaag gccacagaac    360
tgaaacatct tcagtgtcta gaagaagaac tcaaacctct ggaggaagtg ctaaatttag    420
ctcaaagcaa aaactttcac ttaagaccca gggacttaat cagcaatatc aacgtaatag    480
ttctggaact aaagggatct gaaacaacat tcatgtgtga atatgctgat gagacagcaa    540
ccattgtaga atttctgaac agatggatta ccttttgtca agcatcatc tcaacactaa      600 ctggtagatc tcatcatcac catcaccata tcaccggcac ctggtacaac cagctcggct    660
cgaccttcat cgtgaccgcg ggcgccgacg gcgccctgac cggaacctac gagtcggccg    720
tcggcaacgc cgagagccgc tacgtcctga ccggtcgtta cgacagcgcc ccggccaccg    780
acggcagcgg caccgccctc ggttggacgg tggcctggaa gaataactac cgcaacgccc    840
actccgcgac cacgtggagc ggccagtacg tcggcggcgc cgaggcgagg atcaacaccc    900
agtggctgct gacctccggc accaccgagg ccaacgcctg gaagtccacg ctggtcggcc    960
acgacacctt caccaaggtg aagccgtccg ccgcctccga attctgcaga tatccagcac   1020
agtggcggcc gctcgagtct agagggccct tcgaaggtaa gcctatccct aaccctctcc   1080
tcggtctcga ttctacgcgt accggtcatc atcaccatca ccattgagtt taaacccgct   1140
gatcagcctc gactgtgcct tctaaggcct gagctcgctg atcagcctcg atcgaggatc   1200
cagacatgat aagatacatt gatgagtttg gacaaaccac aactagaatg cagtgaaaaa   1260
aatgctttat ttgtgaaatt tgtgatgcta ttgctttatt tgtaaccatt ataagctgca   1320
ataaacaag                                                            1329

<210> SEQ ID NO 5
<211> LENGTH: 1395
<212> TYPE: DNA
<213> ORGANISM: Artificial Sequence
<220> FEATURE:
<223> OTHER INFORMATION: IL-10-SA

<400> SEQUENCE: 5
cgaacgaaag acccgtgtgt aaagccgcgt ttccaaaatg tataaaaccg agagcatctg     60
gccaatgtgc atcagttgtg gtcagcagca aaatcaagtg aatcatctca gtgcaactaa    120 agggggatc cgatctcaat atgaagttat gcatattact ggccgtcgtg gcctttgttg     180
gcctctcgct cggggtaag agatcttctg agaacagctg cacccacttc ccaggcaacc    240
tgcctaacat gcttcgagat ctccgagatg ccttcagcag agtgaagact ttctttcaaa    300
tgaaggatca gctggacaac ttgttgttaa aggagtcctt gctggaggac tttaagggtt    360
acctgggttg ccaagccttg tctgagatga tccagttttaa cctggaggag gtgatgcccc   420
aagctgagaa ccaagaccca gacatcaagg cgcatgtgaa ctccctgggg gagaacctga    480
agaccctcag gctgaggcta cggcgctgtc atcgatttct ccctgtgaa acaagagca     540 aggccgtgga gcaggtgaag aatgccttta ataagctcca agagaaaggc atctacaaag    600
ccatgagtga gtttgacatc ttcatcaact acatagaagc ctacatgaca atgaagatac    660
gaaacagatc tagatctcat catcaccatc accatatcac cggcacctgg tacaaccagc    720
tcggctcgac cttcatcgtg accgcgggcg ccgacggcgc cctgaccgga acctacgagt    780
cggccgtcgg caacgccgag agccgctacg tcctgaccgg tcgttacgac agcgccccgg    840
ccaccgacgg cagcggcacc gccctcggtt ggacggtggc ctggaagaat aactaccgca    900
acgcccactc cgcgaccacg tggagcggcc agtacgtcgg cggcgccgag gcgaggatca    960
acacccagtg gctgctgacc tccggcacca ccgaggccaa cgcctggaag tccacgctgg   1020
```

-continued

```
tcggccacga caccttcacc aaggtgaagc cgtccgccgc ctccgaattc tgcagatatc    1080
cagcacagtg gcggccgctc gagtctagag ggcccttcga aggtaagcct atccctaacc    1140
ctctcctcgg tctcgattct acgcgtaccg gtcatcatca ccatcaccat tgagtttaaa    1200
cccgctgatc agcctcgact gtgccttcta aggcctgagc tcgctgatca gcctcgatcg    1260
aggatccaga catgataaga tacattgatg agtttggaca aaccacaact agaatgcagt    1320
gaaaaaaatg ctttatttgt gaaatttgtg atgctattgc tttatttgta accattataa    1380
gctgcaataa acaag                                                      1395

<210> SEQ ID NO 6
<211> LENGTH: 1566
<212> TYPE: DNA
<213> ORGANISM: Artificial Sequence
<220> FEATURE:
<223> OTHER INFORMATION: SA-CD40L

<400> SEQUENCE: 6
cgaacgaaag acccgtgtgt aaagccgcgt ttccaaaatg tataaaaccg agagcatctg      60
gccaatgtgc atcagttgtg gtcagcagca aaatcaagtg aatcatctca gtgcaactaa     120 agggggatc cgatctcaat atgaagttat gcatattact ggccgtcgtg gcctttgttg     180
gcctctcgct cggggtaag agatctcatc atcaccatca ccatatcacc ggcacctggt     240
acaaccagct cggctcgacc ttcatcgtga ccgcgggcgc cgacggcgcc ctgaccggaa     300
cctacgagtc ggccgtcggc aacgccgaga ccgctacgt cctgaccggt cgttacgaca     360
gcgcccccgc caccgacggc agcggcaccg ccctcggttg gacggtggcc tggaagaata     420
actaccgcaa cgcccactcc gcgaccacgt ggagcggcca gtacgtcggc ggcgccgagg     480
cgaggatcaa cacccagtgg ctgctgacct ccggcaccac cgaggccaac gcctggaagt     540
ccacgctggt cggccacgac accttccacca aggtgaagcc gtccgccgcc tccgaattct     600
tggacaagat agaagatgaa aggaatcttc atgaagattt tgtattcatg aaaacgatac     660
agagatgcaa cacaggagaa agatccttat ccttactgaa ctgtgaggag attaaaagcc     720
agtttgaagg ctttgtgaag gatataatgt taacaaaga ggagacgaag aagaaaaca     780 gctttgaaat gcaaaaggt gatcagaatc tcaaattgc ggcacatgtc ataagtgagg     840
ccagcagtaa aacaacatct gtgttacagt gggctgaaaa aggatactac accatgagca     900
acaacttggt aacctggaa atgggaaac agctgaccgt taaaagacaa ggactctatt     960
atatctatgc caagtcacc ttctgttcca atcgggaagc ttcgagtcaa gctccattta    1020
tagccagcct ctgcctaaag tcccccggta gattcgagag aatcttactc agagctgcaa    1080
atacccacag ttccgccaaa ccttgcgggc aacaatccat tcacttggga ggagtatttg    1140
aattgcaacc aggtgcttcg gtgtttgtca atgtgactga tccaagccaa gtgagccatg    1200
gcactggctt cacgtccttt ggcttactca aactcgaatt ctgcagatat ccagcacagt    1260
ggcggccgct cgagtctaga gggcccttcg aaggtaagcc tatccctaac cctctcctcg    1320
gtctcgattc tacgcgtacc ggtcatcatc accatcacca ttgagtttaa acccgctgat    1380
cagcctcgac tgtgccttct aaggcctgag ctcgctgatc agcctcgatc gaggatccag    1440
acatgataag atacattgat gagtttggac aaaccacaac tagaatgcag tgaaaaaaat    1500
gctttatttg tgaaatttgt gatgctattg ctttatttgt aaccattata agctgcaata    1560
aacaag                                                               1566
```

<210> SEQ ID NO 7
<211> LENGTH: 702
<212> TYPE: DNA
<213> ORGANISM: Artificial Sequence
<220> FEATURE:
<223> OTHER INFORMATION: SA-TNFa

<400> SEQUENCE: 7

```
ccagggctcc aggcggtgct tgttcctcag cctcttctcc ttcctgatcg tggcaggcgc      60
caccacgctc ttctgcctgc tgcactttgg agtgatcggc ccccagaggg aagagtcccc     120
cagggacctc tctctaatca gccctctggc ccaggcagtc agatcatctt ctcgaacccc     180
gagtgacaag cctgtagccc atgttgtagc aaaccctcaa gctgagggc agctccagtg     240 gctgaaccgc cgggccaatg ccctcctggc caatggcgtg gagctgagag ataaccagct     300
ggtggtgcca tcagagggcc tgtacctcat ctactcccag gtcctcttca agggccaagg     360
ctgcccctcc acccatgtgc tcctcaccca caccatcagc cgcatcgccg tctcctacca     420
gaccaaggtc aacctcctct ctgccatcaa gagccctgc cagagggaga ccccagaggg     480
ggctgaggcc aagccctggt atgagcccat ctatctggga gggtcttcc agctggagaa     540 gggtgaccga ctcagcgctg agatcaatcg gcccgactat ctcgactttg ccgagtctgg     600
gcaggtctac tttgggatca ttgccctgtg aggaggacga acatccaacc ttcccaaacg     660
cctcccctgc cccaatccct ttattacccc ctccttcaga ca                       702
```

ALTERATION OF CELL MEMBRANE WITH B7

This application is a U.S. National Stage filing under 35 U.S.C. 371 from International Application No. PCT/US01/20946 filed Jul. 2, 2001 and published in English as WO 02/02751 A2 on Jan. 10, 2002, which claimed priority from U.S. Provisional Application No. 60/215,580 filed Jun. 30, 2000, which applications and publication are incorporated herein by reference.

FIELD OF THE INVENTION

This invention relates to the persistent modification of cell membranes so as to alter the function of the cells. The compositions and methods of this invention achieve effects similar to those of gene therapy without the introduction of exogenous DNA. A useful alteration of cell function is the induction of apoptosis.

BACKGROUND OF THE INVENTION

It has long been the goal of experimental biology and medicine to induce cells to behave in predictable ways and to alter the behavior of cells in ways that are beneficial to a subject. For example, if undesired cells could be induced to alter their behavior to undergo apoptosis while normal cells retain normal function, subjects with a disease caused by proliferation of undesired cells would obtain relief from the disease. Similarly, if tissue-rejecting cells can be eliminated or their behavior changed, transplantation with tissues foreign to the subject can be successful.

Gene therapy has been proposed for selected diseases in order to correct or modify pathological or physiological processes. In gene therapy as it is generally termed, specific DNA is introduced into a tissue and organ, where it is produces various proteins that will correct or ameliorate the condition. It is an unpredictable therapy, depending on potentially dangerous expression vectors and the uncertain efficiency of delivery, which is often low. Moreover, gene therapy is considered to have dangerous side effects, such as sustained expression in desired cells or tissues past the desired duration of therapy, or the introduction of genetic modifications in undesired tissues or cells. Because of such adverse effects, as discovered in human clinical trials, much caution is advised before gene therapy is put in practice.

DNA-based gene therapy has been the subject of intense studies during the past few decades because of the tremendous potential it offers for the treatment of inherited diseases and other pathologic conditions for which the expression of selected proteins may offer treatment. For example, gene therapy can be used for immunomodulation either to enhance the capacity of the immune response to deal with infections or tumors, or to down-regulate the immune response for the prevention of autoimmunity or foreign graft rejection. Despite vast efforts in the past two decades, the safe and effective application of gene therapy to the treatment of diseases has been extremely limited. Among the apparent drawbacks of gene therapy are the possibility of causing permanent change in the DNA complement of the host; uncertain tissue specificity; expression of the encoded protein beyond the intended duration of therapy; and high cost. It would therefore be extremely beneficial if cells and tissues could be modified to express proteins of interest in a short period of time without the introduction of foreign DNA.

Whereas gene therapy has generally focused on the problem of delivering nucleic acids into cells, much fundamental knowledge concerning the important role of cell surface molecules has been gained through studies of signal transduction in cells of the immune response, which are readily accessible and have well-understood functions. The immune response is regulated by the interaction of several different cell types, which react to the presence of foreign antigens. The adaptive immune response is critical to the survival of vertebrates in an environment full of pathogenic microorganisms. Individuals who, due to inborn genetic defects, exposure to chemotherapeutic agents or infection by such viruses as human immunodeficiency virus (HIV), lack a fully functional immune response are susceptible to infections that an individual with a healthy immune response would readily withstand. However, the immune system does not always function in ways that are beneficial to the organism. Its dysregulation leads to autoimmunity and tumors. The immune system also serves as a barrier to the transplantation of foreign grafts, such as cells taken from an individual other than the transplant recipient. Transplantation permits the replacement of failed cells, tissues, or organs in otherwise terminal diseases, while bone marrow transplantation can treat hematopoietic disorders, malignancies, autoimmune disorders, and other diseases. For transplantation to be successful, it is necessary either to suppress the adaptive immunity or to "teach" the recipient's immune system to accept these foreign antigens as native.

The immune response to foreign antigens is initiated by naive T cells that use clonally-expressed T cell receptors (TCRs) to recognize antigens such as peptides presented by self-major histocompatibility complex (MHC) molecules. This recognition reaction, when accompanied by costimulatory signals provided by antigen-presenting cells (APCs), has been thought to result in full T cell activation. A productive T-cell response is now seen as requiring three distinct signals. Signal 1 is generated by T-cell receptor interaction with the major histocompatibility complex (MHC) antigen/peptide on antigen-presenting cells (APCs). Signal 2 is mediated by the engagements of costimulatory molecules, such as B7/CD28 and CD40/CD40L, on T cells and APCs. Signal 3 is transduced via cytokines elaborated by T cells and APCs that have received both Signal 1 and 2. The transduction of these 3 signals drives T cells and APCs to proliferation and differentiation into effectors for the generation of a productive immune response. The lack of any of these signals during the T-cell response results in T-cell anergy and immune nonresponsiveness. For example, tumors evade the immune system by preventing the transduction of one of these signals.

Upon activation, T cells proliferate and differentiate into effector cells that evoke immunological mechanisms responsible for the clearance of antigens from the system. A period of death then follows during which most of the activated T cells undergo apoptosis-mediated "activation-induced cell death" (AICD) and effector activity subsides. Apoptosis is a complex process that involves a series of extra- and intracellular signals that converge on the activation of enzymes called caspases that commit the cell to apoptosis.

Transplantation of foreign cells (such as bone marrow and stem cells), tissues (such as pancreatic islets), and organs (such as kidneys, hearts, livers) has become an important and effective therapeutic alternative for patients with selected terminal diseases. The transplantation of foreign grafts between genetically different patients (allografts between members of the same species or xenografts between members of different species) is, however, limited by the ability to control the immunological recognition and rejection of the graft by the recipient.

Bone marrow (BM) transplantation has been viewed as an extraordinarily promising treatment for hematopoietic and autoimmune disorders and for certain cancers. One obstacle to bone marrow transplantation is the possibility of rejection of the transplanted tissue, mediated by the host's T cells and NK cells. Graft-versus-host-disease (GvHD) is another possible adverse consequence of bone marrow transplantation. Donor T cells in the transplanted tissue can mount an immune response against the host's vital organs, often leading to death of the host. Host-versus-graft reactions and GvHD therefore limit the clinical use of bone marrow transplantation, which might otherwise be widely used to treat various diseases and to prevent foreign graft rejection.

Pharmacological agents that cause immunosuppression are now a mainstay of regimens for the control of allograft rejection. Although such drugs are effective in reducing the severity of rejection episodes, they are nonspecific and fail to create a state of permanent graft-specific tolerance. Continuous exposure of the recipient to these immunosuppressive agents is therefore associated with a significantly increased risk of opportunistic infections and malignancies. The need remains to develop more selective and long-lasting methods to prevent BM rejection.

Additionally, these nonspecific immunosuppressive agents can induce serious and undesirable side effects in the host. These adverse effects often outweigh the benefits for patients with diseases in which the body identifies certain parts of itself as "foreign" and launches an adaptive immune attack that results in autoimmunity, such as is observed in Type I diabetes, arthritis, lupus, and multiple sclerosis. It would be very desirable to be able to "teach" the immune system to tolerate the "foreign" self-antigen.

It would also be very desirable to be able to "teach" the immune system to rid the organism of tumor cells. T cell-mediated cellular immunity is the most critical acquired response against tumors. A series of experimental studies has provided evidence that tumors evade T-cell-mediated immunity by several different mechanisms. These mechanisms include: i) lack of Signal 1, due to inefficient display of MHC/tumor antigen bimolecular complexes on tumor cells or defects in the transduction of this signal; ii) absence of Signal 2, due to the absence of costimulatory molecules on tumor cells; iii) induction of anergy in T cells; and iv) physical elimination of effector T cells via apoptosis. Although all of these mechanisms may be operative in patients with a large tumor burden, the lack of costimulation is believed to play the most critical role.

The need therefore remains to develop more rapid, selective and long-lasting methods to modulate cell function without the introduction of nucleic acids into cells for therapeutic purposes. The need also remains to develop a means of accomplishing the end of gene therapy without many of the risks attendant to the introduction of exogenous nucleic acids into an organism. Since much cell function is controlled through the transduction of signals at the cell surface, a generally applicable method of attaching an agent to a surface would be useful. Among the uses of such a method would be: the modulation of cell function without the introduction of nucleic acids into the cell; the accomplishment of the end of gene therapy by alternative and potentially preferable means; and the manipulation of an organism's immune response in order to diminish that response, as to treat autoimmunity or to forestall graft-versus-host disease, or to increase that response, as to treat tumors or infections.

SUMMARY OF THE INVENTION

The present invention provides a method of modifying a surface, the method comprising: (1) contacting a surface with one member of a binding pair which binds to the surface to form a decorated surface; and subsequently (2) contacting the decorated surface with a composition comprising the second member of the binding pair operably linked to an agent capable of modifying the surface and the function thereof. The binding pair may be avidin/biotin, streptavidin/biotin or antigen/antibody. By "avidin" is meant avidin and any fragment or derivative of avidin which retains strong binding to biotin. By "streptavidin" is meant streptavidin and any fragment or derivation of streptavidin which retains strong binding to biotin. Conversely, by "biotin" is meant any fragment or derivative of biotin which retains strong binding to avidin and streptavidin.

When the surface is a cell surface, the agent may be any compound inducing apoptosis; any agent down-regulating the immune system; any agent up-regulating the immune system; any adhesion molecule for cell tracking; any growth factor; or an antibody ligated to a toxin such as ricin or phytotoxin. When the surface is a cell surface, the contact of step 1 produces a "decorated cell."

When the agent is selected to induce apoptosis, the agent may be a death-inducing molecule such as FasL, mFasL, TRAIL, TNF-a, TWEAK and the like. When the agent is selected to down-regulate the immune system, the agent may be an anti-inflammatory cytokine such as IL-4, IL-10, TGF-$\beta$ and the like. When the agent is selected to up-regulate the immune system, the agent may be a costimulatory molecule such as B7, CD40L and the like or a pro-inflammatory cytokine such as IL-2, IL-12, IL-15, lymphotactin and chemokine.

In a preferred embodiment, the first member of the binding pair is biotin, the second member of the binding pair is a chimeric protein comprising streptavidin and a death-inducing molecule and the surface comprises target cells, tissues, organs or tumors.

In a more preferred embodiment, the first member of the binding pair is Sulfo-NHS-LC-biotin, the second member of the binding pair is SA-mFasL and the surface comprises a cell displaying the Fas receptor. In constructing the second member of the binding pair, streptavidin is fused to the extracellular portion of FasL through recombinant gene technology and the chimeric protein SA-mFasL is produced.

This construct is used in a method to modulate the immune system wherein a subject to be treated is first administered biotin to form decorated cells, followed by administration of SA-mFasL to form chimeric decorated cells. Only those cells in the tissue, organ or tumor which are biotinylated and express Fas will undergo apoptosis. In general, these cells include those cells which cause immuno-mediated injuries.

In another aspect of the invention, a subject who will benefit from down-regulation of the immune system is first administered biotin to form decorated cells and is then administered a construct comprising avidin or streptavidin and a down-regulating molecule. Subjects who will benefit from down-regulation of the immune system include subjects suffering from autoimmunity, graft-versus-host disease, allergies, septic shock and vascular diseases. Subjects undergoing tissue or organ grafts also benefit from the down-regulation of the immune system.

In another aspect of the invention, a subject who will benefit from up-regulation of the immune system is first administered biotin to form decorated cells and is then administered a construct comprising avidin or streptavidin and an up-regulating molecule. Subjects who will benefit from an up-regulation of the immune system include subjects suffering from neoplasia or infectious disease.

In another aspect of the invention, systemic effects are avoided by biotinylating the cells ex vivo by isolation of the target or selection of a target that can be treated topically, followed by reintroduction of the decorated cells into the subject with subsequent second contact.

In another aspect of the invention, the members of the binding pair form a covalent bond with each other. In a preferred aspect, the first member of a binding pair comprises a cysteine residue and the second member of the binding pair comprises a cysteine residue. The two members are first placed together under conditions disfavoring the formation of a disulfide bond between the first member of the binding pair and the second member of the binding pair. In a subsequent step, the two members are placed under conditions favoring the formation of a disulfide bond between the first member of the pair and the second member of the pair.

In another aspect of the invention, the first member of a binding pair contacts a cell surface, a virus, the surface of a glass particle, the surface of a polysaccharide particle or the surface of a plastic particle to form a decorated surface. The decorated surface is then contacted with the second member of the binding pair, to form a second decorated surface. The cell, virus or particle comprising the second decorated surface is contacted with a cell or cell component of an organism either in vitro or in vivo, for the purpose of therapy, diagnosis, cell sorting or identification.

A recombinant nucleic acid is provided comprising the extracellular portion of FasL fused with streptavidin (SA-mFasL). Gene product is provided which is then attached to the cell surface, previously biotinylated in vivo. Methods are taught for the use of gene products for long-lasting elimination of Fas expressing cells.

The methods of this invention can be modified to cause persistent binding of any protein to targeted cells, to mimic the result of DNA gene therapy without modification of the cell genetic material. This persistent binding of a protein to a targeted cell can be considered to be gene therapy at the protein level.

DETAILED DESCRIPTION OF THE INVENTION

Figure 1:
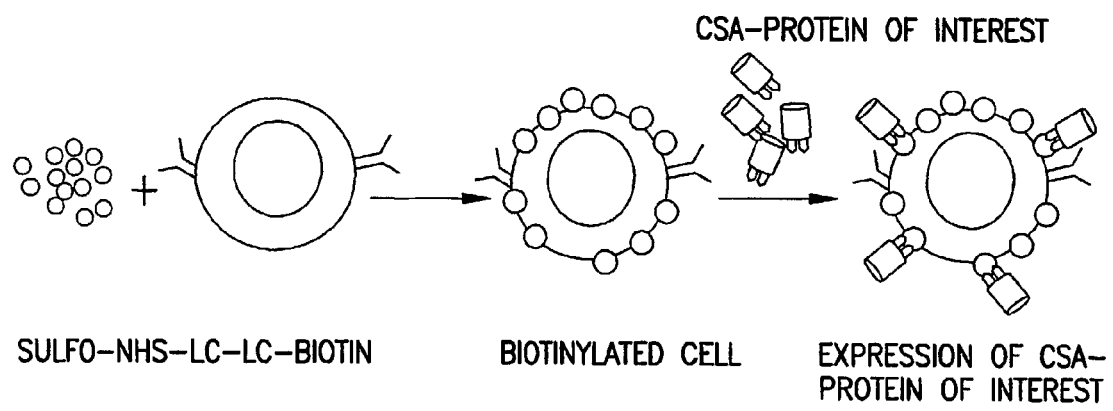
FIG. 1 is a schematic representation of the method to modify cell membrane for the expression of exogenous proteins for new functions.

Because of the noted problems associated with gene therapy as it is commonly used, that is, the introduction and integration of foreign DNA into the genome, a method was sought for the accomplishing the results of gene therapy, that is, long lasting modification of cell function, without the limitations of DNA introduction. The question was raised as to whether the benefits of gene therapy could be obtained by the delivery of exogenous proteins, rather than nucleic acids, to the cells. A method that would safely permit modification of the cell membrane to achieve transient or long-lasting display of therapeutic molecules could have wide-spread application in the clinic. As disclosed in the present application, Applicant has discovered and here discloses such a method, which has the added advantage of rapid cell surface expression.

Because of the thermodynamically favored association of avidin or streptavidin with biotin, the complex formed can modify cell properties for a period that can rival or surpass the duration of the effect elicited by gene therapy that requires the introduction of nucleic acids. The present invention teaches a method of attaching an agent to a surface. Such an agent can be, by way of example and not of limitation, any of a series of immunomodulatory molecules such as death ligands, costimulatory molecules and cytokines. It is useful to attach such agents to surfaces, especially the cell surface, since such agents can be used to physically or functionally eliminate autoreactive, alloreactive, xenoreactive and inflammatory cells to prevent allograft and xenograft rejection, graft-versus-host disease and to treat autoimmunity, septic shock, inflammation, allergies, infections, neoplasias, and vascular diseases. Furthermore, this method can be used to display proteins with defined function on the surface of cells for in vivo trafficking as for the homing of selected hematopoietic cells for therapeutic purposes.

Definitions:

For the purposes of the present application, the following terms have these definitions:

"Agent" means a composition which elicits a measurable biological response or which is useful in the diagnosis, prevention or treatment of a disease or in the sorting or identification of cells, cell components or viruses.

"Binding pair" means two compositions that readily bind to each other; that have affinity for one another; or whose association is thermodynamically and kinetically favored.

"Cell surface" has its normal meaning in the art, comprising the phospholipid bilayer of a cell membranes and the molecules directly or indirectly associated with the bilayer.

"Decorated surface" means a surface to which a member of a binding pair has become bound.

"Expression" means, in addition to its conventional meaning in the art, the placement of a functional protein on or within a cell.

"lastic" means polystyrene, polypropylene, polyethylene or any other polymer capable of being formed into a solid surface.

"Protein" means a protein or polypeptide that is native, non-native, synthetic or modified as by covalent binding.

"Surface" means a cell surface, the surface of a virus, the surface of a particle (e.g., the surface of a glass particle, the surface of a polysaccharide particle, the surface of a plastic particle), the surface of a phospholipid bilayer or the surface of a solid matrix.

"Target cell" means a cell targeted for apoptosis, that is, a cell in which it is desired to induce apoptosis.

An important application of regulation of the immune response is the induction of tolerance to alloantigens, xenoantigens and autoantigens to prevent foreign graft rejection, treat or prevent autoimmunity and GVHD. T cells are the most critical cells of adaptive immunity, which requires, three distinct signals (Signal 1, 2 and 3) for a productive response. Signal 1 is generated by T-cell receptor interaction with the MHC/peptide complex on APCs. Signal 2 is mediated by the engagements of costimulatory molecules, such as B7/CD28 and CD40/CD40L on T cells and APCs. Signal 3 is transduced via cytokines elaborated by T cells and APCs that have received both Signal 1 and 2. The lack of any of these signals during T-cell response to antigens may serve as one of the most effective mechanisms by which tolerance is induced. Upon activation, T cells undergo a state of antigen-driven proliferation that allows up to a 1200-fold clonal expansion. A period of death then ensues during which more than 95% of the activated T cells undergo apoptosis programmed cell death) while the remaining cells differentiate into memory cells as the amount of antigen in the system declines.

Apoptosis or "programmed cell death" plays a central role in both the development and homeostasis of multicellular organisms. Apoptosis can be induced by multiple independent signaling pathways that converge upon a final effector mechanism consisting of multiple interactions between several "death receptors" and their ligands, which belong to the tumor necrosis factor (TNF) receptor/ligand superfamily. The best characterized death receptors are CD95 ("Fas"), TNFR1 (p55), death receptor 3 (DR3 or Apo3/TRAMO), DR4 and DR5 (apo2-TRAIL-R2). A final effector mechanism is mediated by the caspase group of proteins.

In copending International Application PCT.US01/02256, the teachings of which are incorporated by reference, it is disclosed that Fas-/FasL-induced apoptosis plays a central role in protecting immunologically privileged sites, such as the central nervous system, testes and eyes from immune attack. Allogeneic and xenogeneic tissues transplanted into these sites, for instance, are resistant to rejection. Of great importance is the major role apoptosis plays in maintaining homeostasis in the immune system via activation-induced cell death (AICD). AICD is primarily mediated by apoptopic signals transduced by the Fas/FasL interaction. Fas is a 45 kDa, type I, cell surface protein consisting of a cysteine-rich extracellular domain, which transduces a death signal. Fas mediates effector function by interacting with FasL, a type II membrane protein of about 40 kDa. T cells are the primary cell type in the body that express FasL, upon activation. The expression of this molecule makes the activated T cells susceptible to apoptosis, which is induced in an autocrine fashion as Fas engages with FasL on the same cell. Fas on an activated T cell may also interact in a paracrine fashion with FasL on another activated cell. These two pathways of apoptopic T cell death mediated by the Fas/FasL system serve as a homeostatic mechanism for controlling the size of antigen-stimulated T cell clones. Deregulation of this system results in immunological disorders.

The molecular mechanism of Fas/FasL-mediated apoptosis has been studied in great detail. Binding of three FasL molecules with Fas induces trimerization of Fas receptor via c-terminus death domains (dds), which in turn recruit an adapter protein FADD (Fas-associated protein with death domain) and Caspase-8. The oligomerization of this trimolecular complex, Fas/FADD/caspase-8 results in proteolytic cleavage of proenzyme caspase-8 into active caspase-8 that, in turn, initiates the apoptosis process by activating other downstream caspases through proteolysis, including caspase-3.

Apoptosis of activated T cells results in tolerance to allografts and xenografts, including bone marrow and other organ and cellular transplantation. Purging of activated T cells also relieves the symptoms of allergies and other immune-induced diseases. Included in the latter are autoimmune disorders such as multiple sclerosis, lupus erythematosus, sarcoidosis and rheumatoid arthritis. Many disorders, including some tumors, are dependent on lymphocyte functions that lead to persistence of the disorder. Many hematological disorders could be treated with bone marrow stem cell transplants if the immune response could be regulated so as to induce tolerance to the foreign stem cells. Among these disorders are leukemias, lymphomas, aplastic anemia, sickle cell and Cooley's anemia and the like. All of these disorders may be controlled permanently or temporarily by apoptosis of activated immune cells, including T cells.

Strategies are provided for immunomodulation using rapid cell-surface display of proteins, which comprise the construction of chimeric cDNAs encoding the functional portions of an immunoregulatory protein with one member of a binding pair. Table 1 is a summary of such constructs. Choice of constructs may be based on factors such as: the nature of the foreign antigen provoking adaptive immunity; whether the relief to be sought is temporary or permanent; whether a commitment to death is desired or additional downstream regulation of apoptosis is preferred. It is to be understood that the constructs listed below are representative of the invention only and are not limitations. For example, the contructs have been made using core streptavidin (CSA).

Fragments and derivatives of streptavidin as well as the entire streptavidin molecule can be as readily used to make equivalent constructs. Therefore, in the specification, SA is generally used to mean whole, fragmented or derivatized streptavidin. Those skilled in the art can readily, without undue experimentation, follow the teachings of this invention to make constructs comprising a first member of a binding pair and a second member of a binding pair ligated to a known immunomodulatory molecule.

TABLE 1

| Vector | Insert | SEQ ID # | Function | Application |
|---|---|---|---|---|
| pCSA-mFasL | 6His-RS-CSA-SRIPE-Extracellular portion of FasL | 1 | Apoptosis | Induce apoptosis in immune-reactive cells, smooth muscle cells for the treatment of immune-based disorders (GVHD, rejection of foreign grafts, autoimmunity, |

TABLE 1-continued

| Vector | Insert | SEQ ID # | Function | Application |
|---|---|---|---|---|
| | | | | inflammation, allergies, septic shock and likes) and vascular diseases. |
| pCSA-TNFα | 6His-RS-CSA-SRIPE-Extracellular portion of TNFα | 7 | Apoptosis | Induce apoptosis in immune-reactive cells, smooth muscle cells for the treatment of immune-based disorders (GVHD, rejection of foreign grafts, autoimmunity, inflammation, allergies, septic shock and likes) and vascular diseases. |
| pIL-4-CSA | Mature portion of IL-4-6His-RS-CSA-SRIPE | | Immune down-regulation | Down-regulate immune-reactive cells for the treatment of immune-based disorders (GVHD, rejection of foreign grafts, autoimmunity, inflammation, and likes). |
| pIL-10-CSA | Mature portion of IL-10-6His-RS-CSA-SRIPE | 5 | Immune down-regulation | Down-regulate immune-reactive cells for the treatment of immune-based disorders (GVHD, rejection of foreign grafts, autoimmunity, inflammation, and likes). |
| pTGFβ-CSA | Active portion of TGF-β-6His-RS-CSA-SRIPE | 3 | Immune down-regulation | Down-regulate immune-reactive cells for the treatment of immune-based disorders (GVHD, rejection of foreign grafts, autoimmunity, inflammation, allergies, septic shock, and likes). |
| pCyto-CSA | Active portion of other immunoregulatory cytokines-6His-RS-CSA-SRIPE | | Immune down-regulation | Down-regulate immune-reactive cells for the treatment of immune-based disorders (GVHD, rejection of foreign grafts, autoimmunity, inflammation, allergies, septic shock, and likes). |
| pIL-2-CSA | Mature portion of IL-2-6His-RS-CSA-SRIPE | 4 | Immune up-regulation | Up-regulate immune-reactive cells for the treatment of infections and cancers. |
| pB7-CSA | Extracellular portion of B7-6His-RS-CSA-SRIPE | 2 | Immune up-regulation | Up-regulate immune-reactive cells for the treatment of infections and cancers. |
| pCSA-CD40L | 6His-RS-CSA-SRIPE -Extracellular portion of CD40L | 6 | Immune up-regulation | Up-regulate immune-reactive cells for the treatment of infections and cancers. |
| padhesion-CSA | Active portion of adhesion molecules - 6His-RS-CSA-SRIPE | | Immune down- or upregulation | Down-regulate immune-reactive cells for the treatment of immune-based disorders (GVHD, rejection of foreign grafts, autoimmunity, inflammation, allergies, septic shock, and likes). Up-regulate immune-reactive cells for the treatment of infections and cancers. |
| pchemo-kines-CSA | Active portion of immunoregulatory chemokines-6His-RS-CSA-SRIPE | | Immune down- or upregulation | Down-regulate immune-reactive cells for the treatment of immune-based disorders (GVHD, rejection of foreign grafts, autoimmunity, inflammation, allergies, septic shock, and likes). Up-regulate immune-reactive cells for the treatment of infections and cancers. |

A preferred production cell for the production of chimeric compositions encoded by the DNA constructs is the *Drosophila* system that is commercially available. However, those skilled in the art of producing chimeric compositions will recognize that many other expression systems and vectors are suitable for production of the chimeric compositions of this invention. Included in these other systems are *Escherichia coli*, yeast and mammalian cell cultures.

The inventions disclosed in copending international application PCT/US00/34554, the teachings of which are hereby incorporated by reference, are directed to the apoptosis of lymphocytes and tumor cells. The present invention discloses an improved method of expressing immunomodulatory molecules with therapeutic interest on the surface of cells via binding pair coupling. Avidin or streptavidinibiotin is an example of a binding pair useful in the present invention. A modified FasL protein is described in detail as an example of such a composition. Bone marrow cells, endothelial cells, splenocytes, tissues such as pancreatic islets and organs such as hearts are examples of cells amenable to cell surface alteration. It has now been found that this method can be used to down-regulate or up-regulate immune responses to antigens. This method, therefore can be used for the prevention of foreign graft rejection, for the prevention or treatment of autoimmunity and the up-regulation of immune response to tumors and infections. Additionally, it is provided that proteins other than those with immunoregulatory functions can be bound to cells without causing systemic side effects.

The invention will now be described with specific examples. The experimental procedures described herein are representative of compositions and methods for persistent binding "expression" of agents to cells, tissues or organs. One embodiment specifically described is a chimeric composition, SA-mFasL, produced by fusion of DNA coding for core streptavidin protein with that of DNA coding for FasL and expressing the chimeric composition (SEQ#1) in a suitable production cell.

The target cells are first biotinylated ex vivo or in vivo and then SA-mFasL is administered in order to cause apoptosis, resulting in, for example, induction of donor-specific long-term survival and/or tolerance. Another example that is described in detail is the transplantation of pancreatic islet cells along with immune cells treated according to the methods of this invention, with subsequent enduring pancreatic insulin production. Another example is the long term survival of ectopic heart transplants. Others examples are also provided. Following the teachings of the following examples, one skilled in the art can readily apply these to alter the membrane function of other cells.

Alternatively, the DNA encoding such chimeric compositions may be applied ex vivo or in vivo, leading to permanent changes such as the apoptosis of activated T cells.

The following examples are disclosed in order to illustrate the present invention as it is applied in practice and do not limit the scope of the appended claims.

EXAMPLE 1

Cloning of Core Streptavidin for the Generation of Chimeric Proteins.

The present invention discloses technology for cell-surface modifications to express exogenous proteins without the introduction of nucleic acids into cells and comprises: i) generation of a chimeric molecule consisting of core streptavidin and functional domains of a desired protein, ii) modification of the cell membrane with biotin, and iii) decoration of the biotinylated cells with the chimeric molecule (FIG. 1). To accomplish this, genomic DNA encoding streptavidin was cloned from *S. avidinii* using specific primers in PCR. 5' and 3' primers were designed to incorporate sequences for selected restriction enzyme sites and amino acids that allow three dimensional flexibility, proper folding and function. The gene was cloned into the TA cloning vector, sequenced and subcloned into the pMT/Bip/V5-HisA vector for expression in a high-yield insect expression system (DES™, Invitrogen).

EXAMPLE 2

Construction of Chimeric Genes for Expression in Production Cells.

Figure 2:
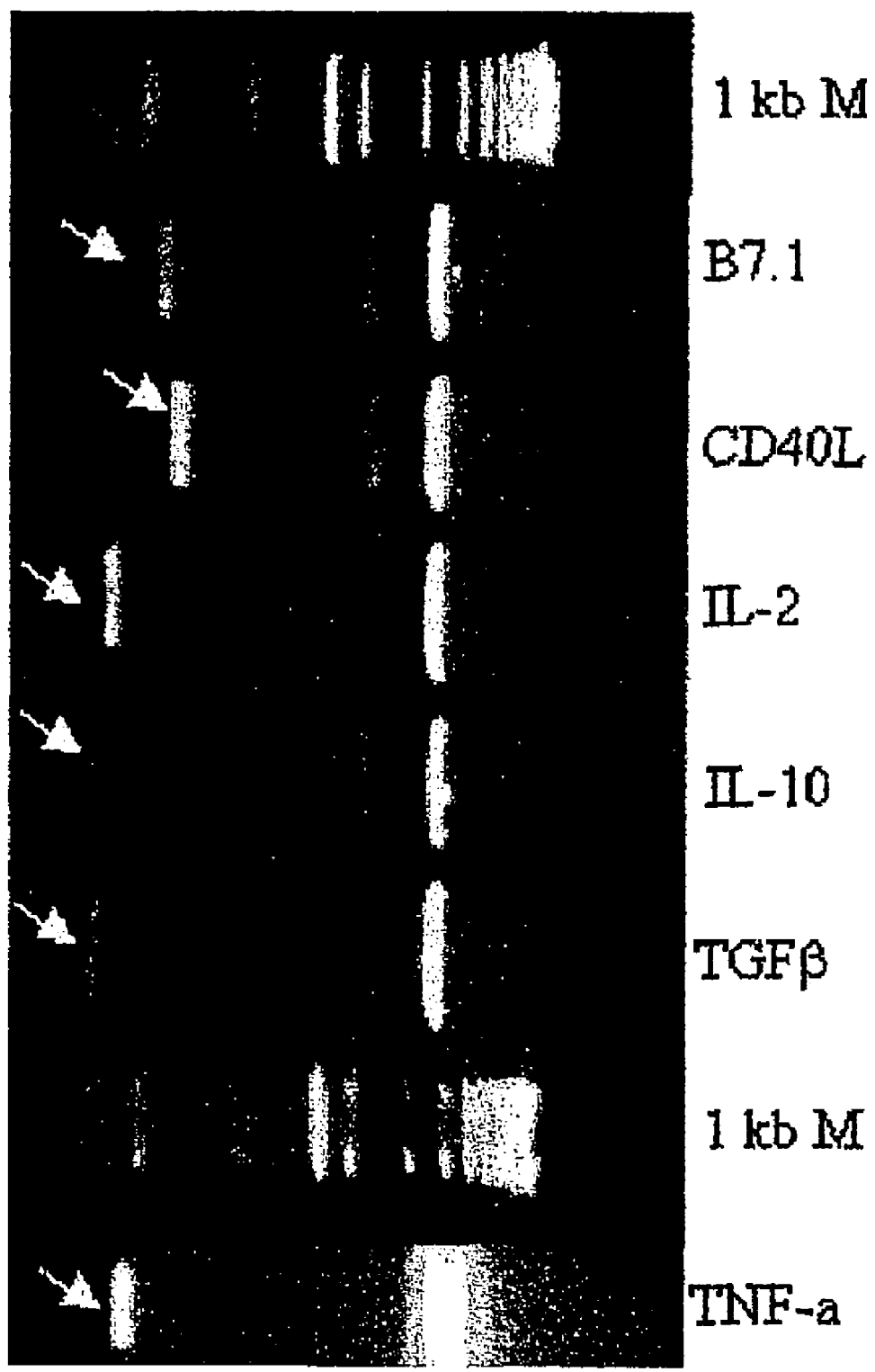
FIG. 2 shows the restriction fragment analysis of the expression vector containing the indicated clones.

Total RNA was prepared from human cell lines or peripheral blood cells and 2 ng of this RNA was reverse transcribed into the first strand of DNA using oligo (dT) 18 as a primer for reverse transcriptase. One-tenth of this cDNA preparation was then amplified, using three sets of sense and antisense primers specific for human IL-2, IL-4, IL-10, TGF-β, FasL, TNF-α, B7.1, and CD40L in 8 separate PCR amplifications. The 5' and 3' primers were designed to include restriction enzyme sites for cloning and several amino acid residues to facilitate the proper folding of the product. These primers amplified DNA bands of expected sizes for all these genes of interest. These PCR products were then cloned into the TA cloning vector (Invitrogen, San Diego, Calif.) and a library prepared from this material was screened using the same oligonucleotide primers in PCR amplifications. The positive clones were digested with appropriate restriction enzymes, leading to the release of expected size of fragment for each gene (FIG. 2) shown in Table 1. All indicated clones were sequenced and found to have the expected characteristics. These clones were then fused to CSA in the pMT/Bip/V5-HisA vector either as N-terminus or C-terminus proteins to facilitate correct three dimensional structure and function (see SEQ IDs in Table 1).

Chimeric proteins were subcloned in frame with the *Drosophila* BiP secretion signal in the pMT/BipNV5-HisA vector for expression in a high-yield insect expression system (DES™, Invitrogen). Recombinant vectors were transiently transfected into Drosophila S2 cells using calcium phosphate. Cells were then pulsed with copper sulfate to activate the inducible metallothionein promoter driving the expression of chimeric proteins. Culture medium was collected at various times post-activation, dialyzed to remove the copper sulfate, and analyzed for chimeric proteins using ELISA and Western blot.

EXAMPLE 3

Biotinylation of Cells, Expression of Recombinant Proteins, and Time Kinetics of Expression in Vitro The therapeutic use of this protein-based approach requires successful biotinylation of cells, tissues, or organs under physiological conditions and attachment to these cells chimeric proteins consisting of CSA and molecules with therapeutic potential (FIG. 1).

The optimum conditions for biotinylation were first determined. Single cell suspensions were prepared from spleen or bone marrow of the rat. One million cells were incubated in various concentrations, ranging from 1.5 to 150 μM, of EZ-Link biotin (trade name of Sulfo-NHS-LC-biotin, Pierce, Rockford, Ill.) in saline at room temperature for 30 minutes. After extensive washing to remove free biotin, cells were either cultured or used for staining with fluorescein (APC)-labeled streptavidin in order to assess the level of biotinylation. 100% of the cells were positive for biotin at 5 µM biotin concentration (data not shown).

To determine how long biotin persists on actively dividing cells and the optimum dose of biotin (15 µM), biotinylated splenocytes were cultured in the presence of a T cell mitogen, concanavalin A (ConA), to stimulate T-cell proliferation. ConA-stimulated and unstimulated cells were harvested at various times post culture and stained with APC-streptavidin and analyzed by flow cytometry. Splenocytes without streptavidin and splenocytes with biotin alone served as background staining. Over 50% of the cells maintained biotin on the surface for 20 days, the longest time point tested. A significant portion (>35%) of actively dividing cells also expressed biotin at this time period. It was next tested to determine whether biotinylation interferes with the proliferation of splenocytes. Splenocytes were activated with 2.5 µg/ml ConA for various days in 96-titer plates. Cultures were pulsed with tritiated thymidine, harvested, and analyzed for DNA-associated radioactivity as an indication of proliferation. Biotinylated splenocytes proliferated in response to ConA activation with similar kinetics and levels as compared with unmanipulated splenocytes, suggesting that biotinylation at concentrations ranging between 1.5–15 µM does not have a significant effect on the proliferative function of the cells (data not shown).

Biotinylated vascular endothelial cells in culture were tested to determine the time kinetics of biotin on the cell surface. The rationale for this set of experiments is to test how long biotin persists on the surface of differentiated cells with minimal turnover in tissues such as heart vasculature. Monolayer cultures of rat aortic endothelial cells were treated with 15 µM concentration of biotin in six-well plates for 30 min at room temperature. Cells were extensively washed and one well of the culture was digested with trypsin at different times post biotinylation, single cell suspension was prepared and analyzed in flow cytometry using APC-streptavidin. A significant portion of endothelial cells (>15%) expressed biotin 20 days in culture, the longest time point tested.

Figure 4:
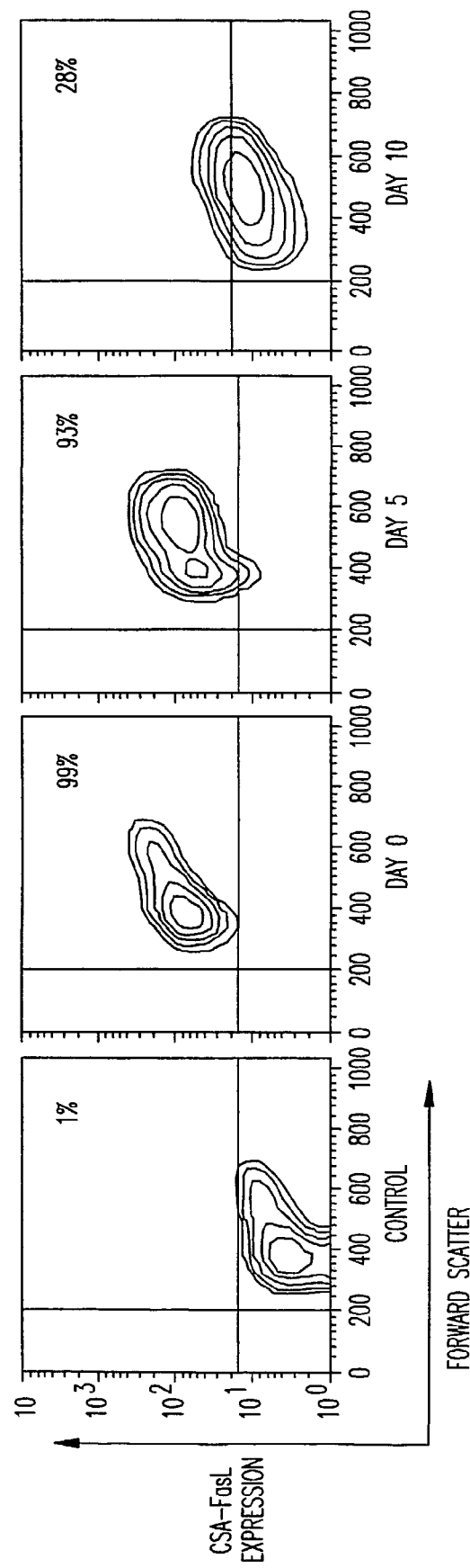
FIG. 4 shows the in vitro expression of SA-mFasL on the surface of splenocytes.

Splenocytes were tested for the expression of one of the recombinant proteins with immunomodulatory function, the extracellular portion of FasL fused with core streptavidin (SA-mFasL). Splenocytes were biotinylated as stated above, incubated with 100 ng SA-mFasL for 20 min, and maintained in a 37° C. incubator for defined periods of time at which cells were stained with an anti-FasL antibody. Almost all the cells expressed SA-mFasL on day 5 and significant number of cells (>25%) expressed SA-mFasL on day 10, the last time point analyzed (FIG. 4).

Figure 5:
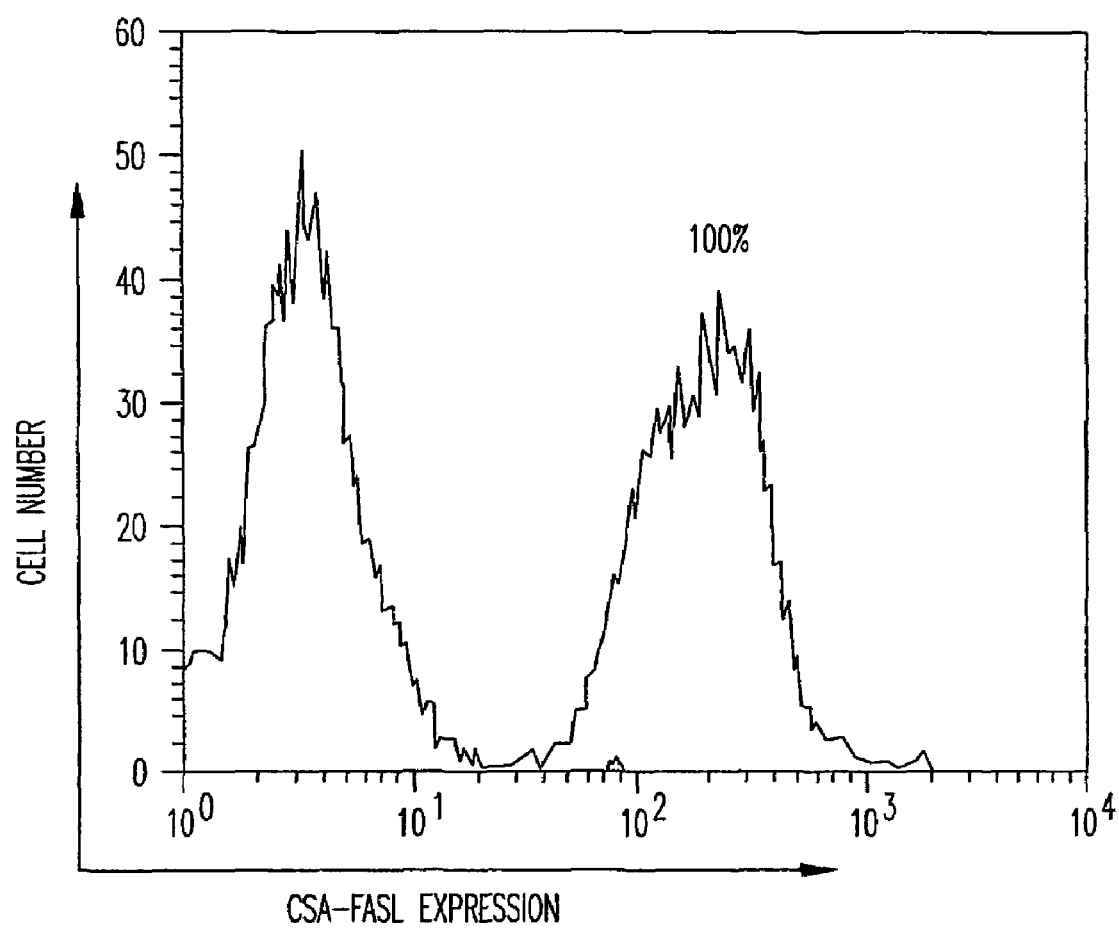
FIG. 5 shows SA-mFasL expression on the surface of bone marrow cells.

One of the objectives of the proposed protein-based gene therapy to use immunomodulatory molecules such as SA-mFasL to facilitate the engraftment of BM cells in a foreign environment. Therefore, BM cells were tested for biotinylation and expression of FasL at the protein level. BM cells were harvested from femurs and tibia of rats using standard protocols. Single cells suspension was prepared and then biotinylated under the above conditions. After extensive washing to remove biotin, BM cells were treated with SA-mFasL (50 ng/million cells) for 20 min on ice. Cells were then washed extensively to remove the free SA-mFasL and stained with an antibody against FasL (PE-MFL4) in flow cytometry. As shown in FIG. 5, 100% of the BM cells expressed SA-mFasL.

EXAMPLE 4

Time Kinetics of Expression in Vivo

Figure 3:
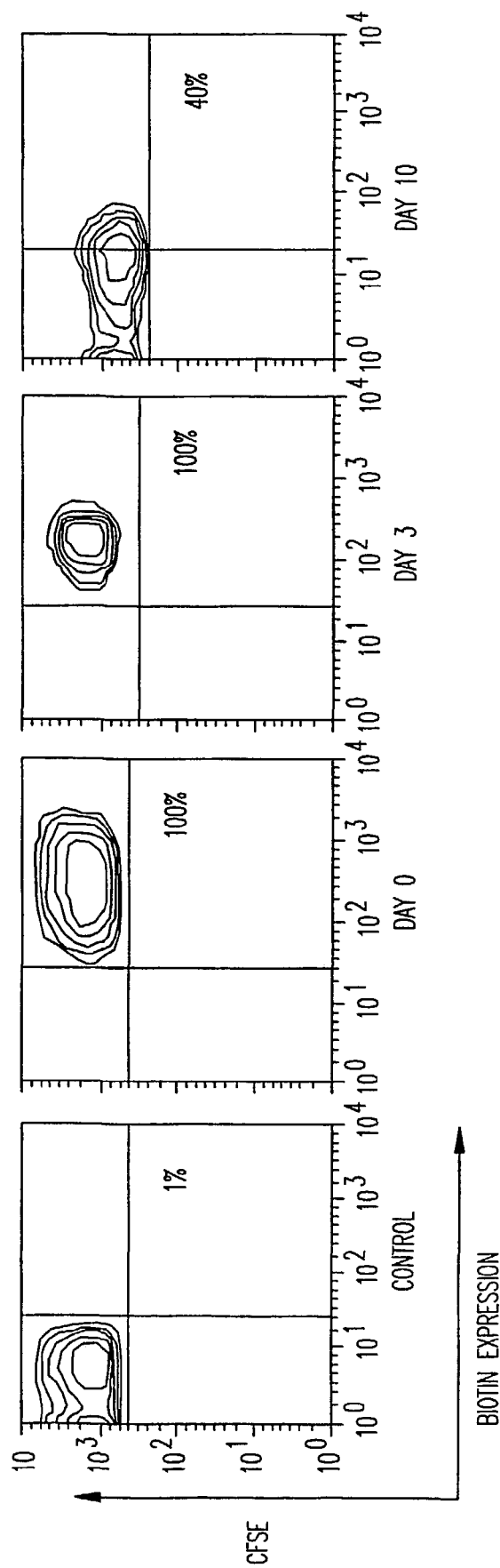
FIG. 3 shows biotin expression in vivo.

Splenocytes were labeled with a lipophilic dye (CFSE), which incorporates and persists in the cell membrane for an extended period of time in vivo, modified to express biotin or SA-mFasL, and injected into syngeneic animals intravenously. Splenocytes were harvested at various times post injection and stained with APC-streptavidin or anti-FasL antibody for analysis in flow cytometry. As shown in FIG. 3, biotin was detected on the surface of 40% of CFSE positive cells 10 days after in vivo injection, the latest time point tested. Similarly, CFSE positive cells modified to express SA-mFasL were positive (26%) for the expression of this molecule 5 days after injection. Taken together, these data clearly demonstrate that this approach allows for the expression of proteins for an extended period of times in vivo to perform function of interest.

EXAMPLE 5

Blocking of Alloreactive Immune Response in Vitro Using Target Cells Expressing Immunomodulatory Molecules To test whether cells modified to express immunomodulatory proteins of interest using this approach can be used to prevent alloreactive responses, allogeneic splenocytes were modified to express SA-mFasL and used as targets in in vitro proliferation assays. Briefly, splenocytes from F344 rats were biotinylated, treated with culture supernatants or purified SA-mFasL. Supernatant from cells transfected with a nonfunctional construct served as control and are referred to as S2 supernatant throughout this application. These cells were then irradiated and used as stimulators for alloreactive responses in a standard five-day mixed lymphocyte culture. Lymphocytes harvested from the lymph nodes of PVG.IU rats were used as responders. Targets expressing SA-mFasL completely blocked the proliferative response of lymphocytes as compared to culture without SA-mFasL. These data demonstrate that biotinylated splenocytes can serve as antigen-presenting cells and that SA-mFasL expressed on the surface of splenocytes block an alloreactive immune response in vitro. Additionally, these data demonstrate that biotinylation does not interfere with the antigen-presenting function of cells since cells decorated with biotin and treated with S2 control supernatants did not interfere with their capacity to stimulate lymphocytes. These data, therefore, demonstrate that expression of the proteins on the surface of cells does not interfere with the function of cells nor the expressed molecules. This is a critical step in validating protein-based expression as a means of immune regulation.

EXAMPLE 6

Toxicity of SA-mFasL Protein.

In general, most cells that express Fas are activated, such as activated lymphocytes, or fast-dividing, such as hepatocytes, or undesirable, such as tumor cells. However, it had to be asked whether SA-mFasL might be toxic. It has been shown that antibodies against Fas induce fulminant liver damage in selected mouse strains when injected intravenously or intraperitoneally. This is believed to be due to the expression of Fas on hepatocytes. In order to ascertain whether the chimeric protein of this invention was likewise toxic, rats were injected intraperitoneally or intravenously with $2 \times 10^7$ splenocytes bearing biotin-SA-mFasL or $8 \times 10^7$ bone marrow cells bearing biotin-SA-mFasL intravenously. The animals were closely monitored for 10 days and then sacrificed for gross pathological and anatomical analysis. No noticeable pathology was found in animals injected with cell-biotin-SA-mFasL as shown in Table 2.

TABLE 2

| Group | Number | Cells | Route of injection | Side effects |
|---|---|---|---|---|
| I | 3 | $2 \times 10^7$ splenocytes-bio | intraperitoneal | none |
| II | 3 | $2 \times 10^7$ sp.-bio-SA-mFasL | intraperitoneal | none |
| III | 3 | $8 \times 10^7$ bone-marrow-bio | intravenous | none |
| IV | 3 | $8 \times 10^7$ bone-marrow-bio-SA-mFasL | intravenous | none |

EXAMPLE 7

FasL Expressing BM Cells Rescue Lethally Irradiated Rats

Figure 6:
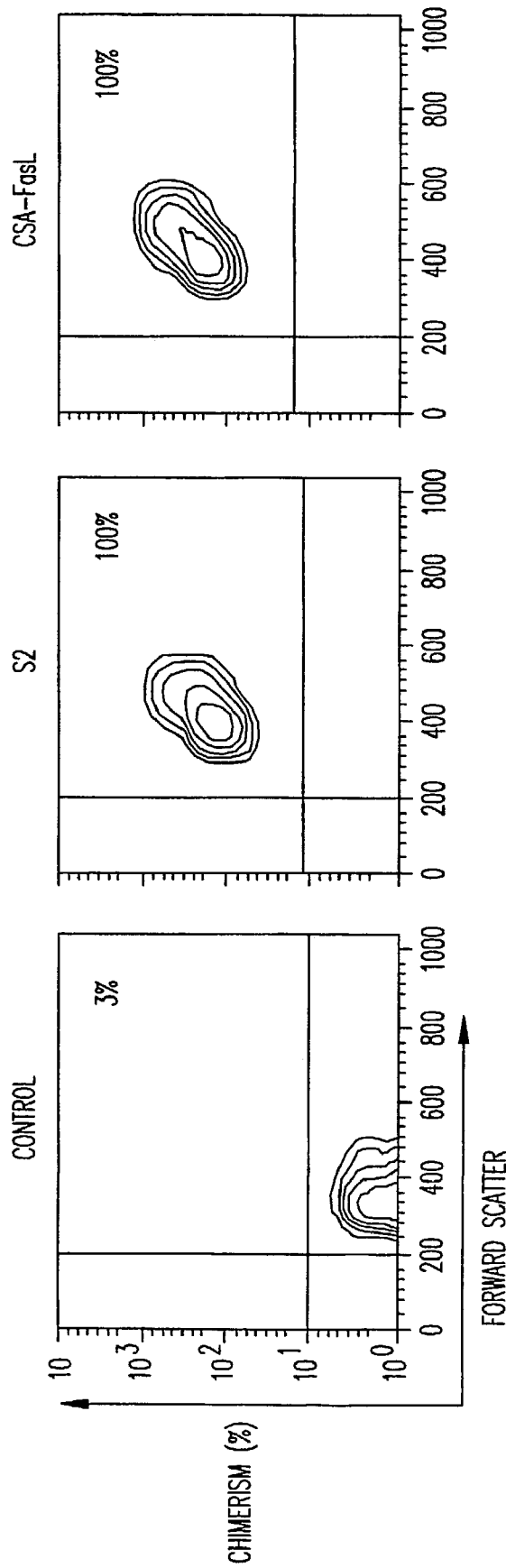
FIG. 6 shows donor chimerism in lethally irradiated animals.

The major premise of this approach is to use protein-based expression as an alternative to DNA-based gene therapy. Prevention of BM cell rejection by this approach of modifying BM cells for immune evasion will suffice for this condition. Bone marrow cells were harvested from PVG.R8 or ACI rats, modified to express biotin or SA-mFasL, and administered i.v. at $0.7-1 \times 10^8$ cells/animal into lethally (950 cGy) irradiated rats. Irradiated animals receiving no cells served as controls. All the animals receiving no cells expired within 8–9 days (n=6) whereas all the animals (n=12) receiving BM cells manipulated to express bio or SA-mFasL were 100% chimeric (FIG. 6) and survived indefinitely (>100 days). These data clearly demonstrate that BM cells are safely manipulated by this novel approach to express proteins of interest for therapeutic purposes without affecting their long-term engraftment capacity.

EXAMPLE 8

SA-mFasL Expressing BM Cells Block Alloreactive Responses in Vivo

Figure 7:
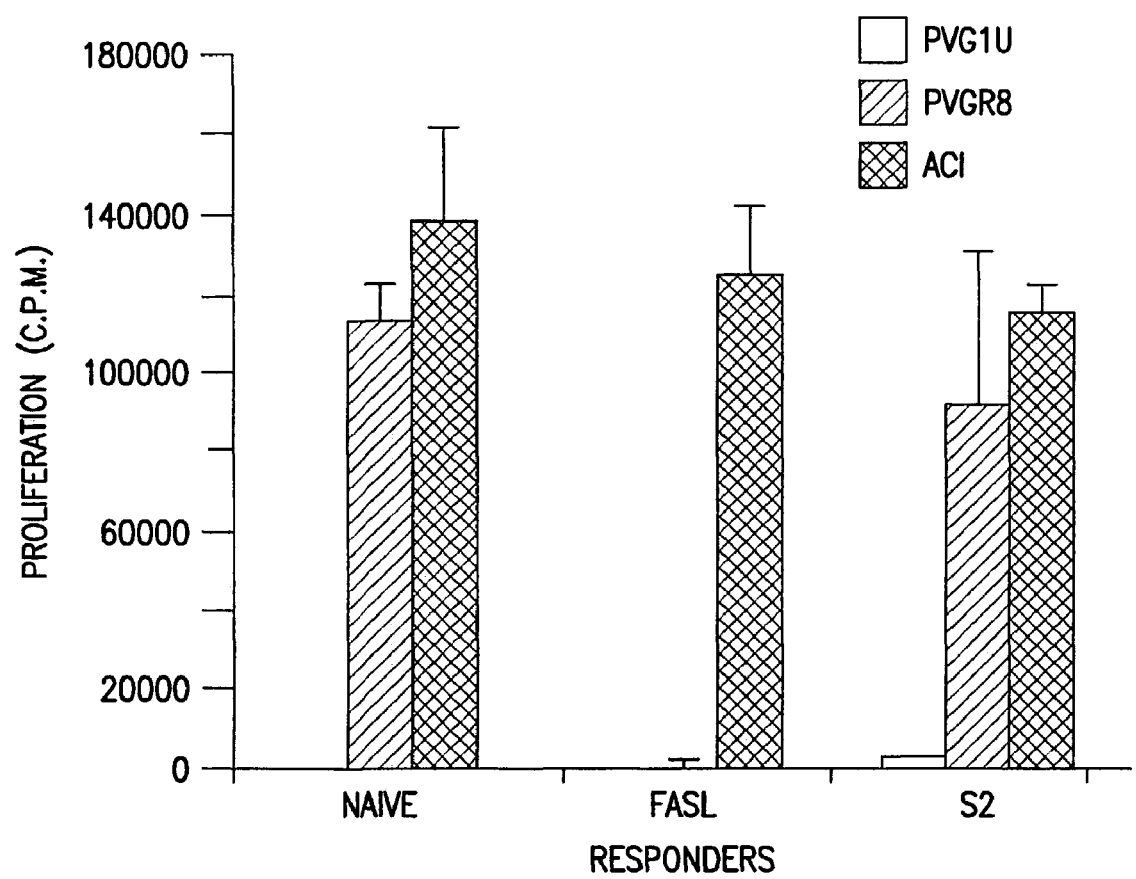
FIG. 7 shows a graphic summary of allogeneic cells decorated with SA-mFasL blocking in vivo alloreactive responses.

BM cells expressing an immunomodulatory molecule such as SA-mFasL were used to induce allotolerance as target cells in vivo. PVG.1U or WF rats were administered i.v. with $0.7-2 \times 10^8$ PVG.R8 or ACI BM cells, respectively, expressing FasL or biotinylated cells treated with control S2 supernatant. Mesenteric lymph nodes were harvested 60 days after injection and used as responders to PVG.R8 or ACI cells in a standard mixed lymphocyte assay. There was a complete absence of response to donor antigens. This in vivo immune nonresponsiveness was donor specific as the response to third party antigens was intact. This effect was SA-mFasL-specific as animals receiving PVG.R8 cells treated with control S2 supernatant generated a normal response to donor as well as third party antigens as compared with the response of naïve animals (FIG. 7). These data validates the in vitro blocking observation and provide direct evidence for the immunomodulatory effect of this approach in vivo.

EXAMPLE 9

Modification of Heart to Express CSA-Protein on Vascular Endothelium

The methods of the present invention have been applied to effect protein-based expression on organs. Modification of organs, rather than the host, ex vivo to express proteins of interest presents a desired therapeutic approach in selected settings. Ex vivo manipulation avoids complications that may arise if the host were treated, and which may include, but are not limited to, undesirable side effects. Therefore, the heart was used as a test system to express biotin, streptavidin, and SA-mFasL in ACI rats and B10.BR mice at 37° C. Briefly, the aortas of excised hearts were cannulated and perfused in a Langendorff retrograde perfusion system at a pressure of 96 mmHg with modified Krebs-Henseleit solution (KH). Cardiac contraction force was monitored with a latex balloon introduced into the left ventricle. The perfusion protocol for rat hearts was: 20 min with KH to allow stabilization of cardiac function; 20 min KH containing 5 μg/ml EZ-Link Sulfo-NHS-Biotin (Pierce); 10 min KH for biotin washout; 20 min KH containing 0.5 μg/ml of either Streptavidin-FITC (Zymed) or SA-mFasL; 10 min KH for streptavidin washout. Control hearts were perfused with KH solution only. Left ventricular pressure decreased during 80 min of perfusion from 98±7 to 91±6 mmHg in all three groups (n=5/group). Coronary flow did not decrease significantly from baseline values of 10.4±0.6 ml/min (n=15). These data indicate that endothelial biotinylation and decoration with SA-mFasL have no short-term detrimental effect on cardiac function and that FasL is not directly toxic to the coronary arteries.

It was next determined whether biotinylated endothelial lining of the coronary arteries can be "decorated" with SA-mFasL at 4° C. This temperature is widely used in the clinical setting for extracorporeal cardiac preservation before transplantation. Mouse (B10.BR) and rat (ACI) hearts were arrested with a magnesium cardioplegic solution (KH+16 mM $MgSO_4$) and were perfused at 4° C. according to the protocol delineated above (biotin, KH, streptavidin-FITC or SA-mFasL, KH). Biotin on vascular endothelium was detected by streptavidin-FITC whereas SA-mFasL was detected using antibodies against streptavidin (Zymed) and FasL (MFL4) as primary and FITC-labeled proper secondary antibodies. Hearts were removed and frozen at −80° C. on the stage of a modified microtome (Polycut S, Reichert-Jung). Sequential cryosections (~200 micron) were performed and the presence of FITC-labeled streptavidin or antibodies was determined with an Axiopan microscope (C. Zeiss). The stage of the microscope was modified to accept the cooling block of the microtome. Images of cardiac sections were acquired at a magnification of 10×. Fluorescence was detected in cardiac vasculature, demonstrating the feasibility of biotin and streptavidin conjugation to vascular endothelium under hypothermic conditions, in a preservation medium widely used in clinical practice. The presence of SA-mFasL in the graft endothelium perfused with SA-mFasL, but not control S2 supernatant, was verified using FITC-MFL4 mAb. These data show that SA-mFasL can be introduced into coronary arteries via biotinylation in conditions of extracorporeal organ preservation. Manipulation of the graft as described above is performed within 10–60 min, at 4° C., using a standard preservation solution. Thus, this approach meets the requirements of temperature, duration, and conditions used in the clinic.

EXAMPLE 10

Hearts Modified to Express Biotin or SA-mFasL Survived Indefinitely when Transferred into Syngeneic Host.

The question arose whether this protein-based modification of organs affects the function. Hearts modified to express bio or SA-mFasL were heterotopically transplanted into syngeneic recipients. Graft survival was assessed by daily abdominal palpation of the grafted heart. As shown in Table 3, there was no detectable difference between the survival of graft recipients transplanted with syngeneic hearts decorated with SA-mFasL (n=4;>56 days) or KH-perfused control syngeneic hearts (n=4;>74 days).

TABLE 3

Survival of heart grafts expressing SA-mFasL

| Group | Recipient | N | Donor | Treatment | Rejection time (days) | MST |
|---|---|---|---|---|---|---|
| A | BALB/c | 5 | BALB/c | — | >100, >100, >100, >100, >100 | >100 |
| B | BALB/c | 4 | BALB/c | Perfusion | >74, >74, >88, >88 | >74 |
| C | BALB/c | 4 | BALB/c | Perfusion + SA- | >56, >56, >68, >68 | >56 |

EXAMPLE 11

Chimeric Decorated Islet Cells.

Figure 8:
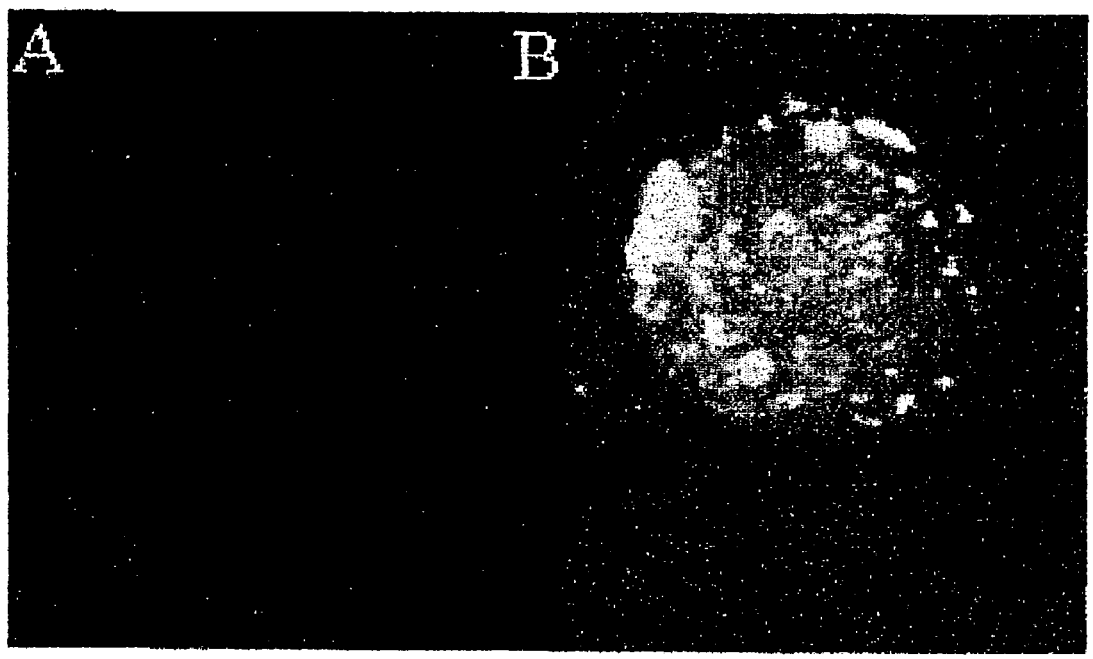
FIG. 8 shows a pancreatic islet cell expressing FasL (red) and streptavidin (B) compared to a control islet (A).
Figure 9:
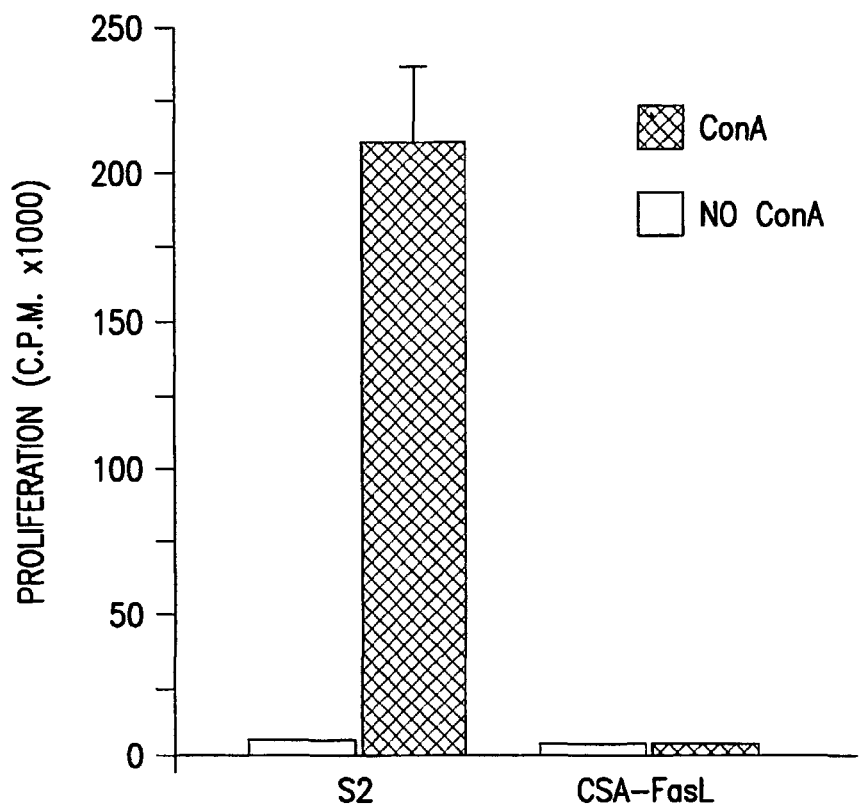
FIG. 9 shows T cells modified to express SA-mFasL, activated by ConA.

Pancreatic islet transplantation is widely contemplated for the correction of diabetes. To test whether the methods of this invention can be effective for the prevention of rejection of islet allografts, diabetes was induced in BALB/c recipients by intraperitoneal injection of streptozin (260 mg/kg). Animals demonstrating blood glucose levels>450 mg/d1 for at least three consecutive days were used as recipients of minor+major histocompatibility antigens-disparate C57BL/10 islets. Islets were harvested from C57BL/10 mice and isolated on a Ficoll gradient according to standard protocol. Splenocytes were harvested from C57BL/10, biotinylated (15 µM), decorated with FasL or control supernatant, and irradiated (2000 rads). One million of splenocytes were cotransplanted with ~400 islet cells under the kidney capsule of diabetic Balb/c mice. Survival and function of the islets were assessed by monitoring blood glucose levels starting three days after transplantation. FasL-decorated splenocytes prolonged the survival of all allogeneic islets beyond nine days, the date at which the glucose levels of control mice had risen to near the pretransplantation level. FIG. 8 shows a pancreatic cell expressing FasL and streptavidin.

In a further example of this technique, mouse pancreatic islets were harvested by digestion with collagenase and purified using Ficoll gradients. Islets were cultured overnight and then modified with biotin (5 µM) and decorated with SA-mFasL (~100 mng/ml) or S2 supernatant as control. Inspection of islets by confocal microscopy showed high levels of biotin and SA-mFasL. Islets decorated with SA-mFasL remained viable in culture for over 10 days as determined by visual inspection and trypan blue exclusion.

Taken together, these data clearly demonstrate that cells, tissues, and complex organs, such as hearts, can be modified with biotin to display proteins chimeric with streptavidin for extended periods of time without detectable toxicity.

EXAMPLE 12

Prevention of GVHD.

Bone marrow transplantation (BMT) has the potential to treat a variety of genetically inherited and acquired hematological disorders, induce tolerance to autoimmune antigens and foreign grafts. BMT is, therefore, perceived as a natural way of performing gene therapy. The major complication is, however, graft-versus-host disease, which is fatal in most instances. T cells are considered to be the most important cells to cause GVHD. A method allowing specific elimination of T cells in the BM inoculum that cause GVHD has wide-spread clinical application. Conventional gene therapy has been used to introduce "suicide" genes into T cells. Once GVHD occurred, the suicide machinery was activated to eliminate these cells. The obstacles of conventional gene therapy, however, are major problems for routine use of this approach in clinics. A more "noninvasive" approach is needed to achieve this "suicide" approach.

Figure 10:
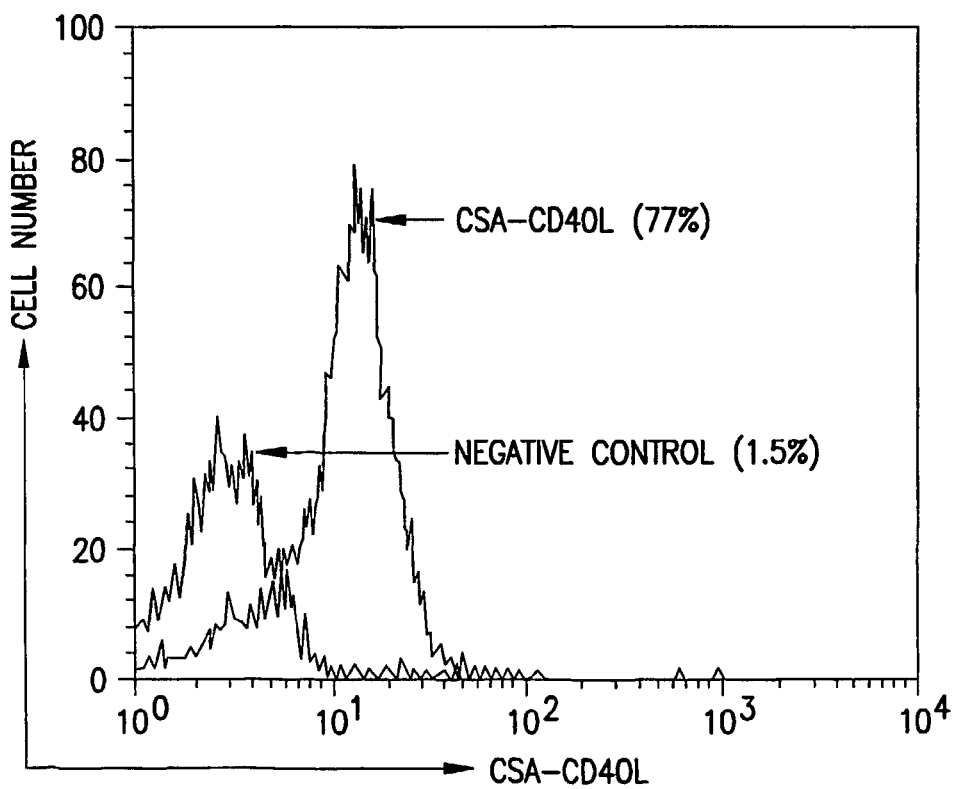
FIG. 10 shows expression of SA-CD40L on splenocytes.

This methods of the present invention are well suited for the "suicide" approach or immune down-regulation. Display of apoptotic (death ligands) or down-regulatory molecules (anti-inflammatory cytokines; CSA-IL-4, IL-10, TGF-β) in bone marrow cells (including mature T cells) are anticipated to physically or functionally eliminate these cells upon their recognition of host antigens and activation. As a proof of concept, it was shown that T cells in splenocytes modified to display SA-mFasL did not generate a proliferative response when stimulated with T-cell mitogens (FIG. 10). In contrast, unmodified splenocytes generated a vigorous proliferative response, demonstrating that T cells responding to mitogens expressed Fas and died upon the interaction of FasL with Fas on the same cell (suicide). It was further demonstrated that rats receiving bone marrow cells and mature lymphocytes developed GVHD within 17–20 days. Treatment of these animals with syngeneic splenocytes expressing FasL resulted in the prevention of GVHD, strong in vivo data that this approach is superior to other treatment regimens that are used in the clinic.

EXAMPLE 13

Immune Down-Regulation Using Immunomodulatory Molecules.

The methods of the present invention of expressing exogenous proteins on the cells, tissues, and organs are made particularly effective in down-regulating the immune system for therapeutic purposes when several of these molecules are expressed simultaneously. Therefore, a combination of death ligands (SA-mFasL, -TNFα, -TRAIL and likes) and anti-inflammatory molecules (CSA-IL-4, IL-10, -TGF-β and likes) are expressed on the surface of cells, tissues, and organs as a therapeutic approach to prevent/treat autoimmune disease, foreign graft rejection, and other immune-based disorders. This method shows down-regulation of the immune system.

EXAMPLE 14

Vaccination Against Tumors.

Tumors may evade the immune system by down-regulating the signals that provoke a T-cell response. An effective T-cell response requires three distinct signals: Signal 1, 2, and 3. Signal 1 is generated by T-cell receptor interaction with the major histocompatiblity complex (MHC) anti-peptide on antigen-presenting cells (APCs). Signal 2 is mediated by the engagements of costimulatory molecules, such as B7/CD28 and CD40/CD40L, on T cells and APCs. Signal 3 is transduced via cytokines elaborated by T cells and APCs that have received both Signal 1 and 2. The transduction of these three signals drives T cells and APCs to proliferation and differentiation into effectors for the generation of a productive immune response. The lack of any of these signals during T cell response to tumors may serve as one the most effective mechanisms by which tumors evade the immune system. The present invention provides methods and compositions to modify cell surface for the expression of exogenous proteins. This approach is aimed at converting any cells into professional antigen-presenting cells for the generation of an effective immune response.

A chimeric protein composed of CSA and extracellular portion of CD40L with engineered synthetic residues for structural flexibility (CSA-CD40L) was produced in Drosophila production cells. This molecule was then used for expression on the surface of splenocytes. Almost all the splenocytes were positive for CSA-CD40L as shown by an antibody against CD40L in flow cytometry (FIG. 11). Splenocytes expressing CD40L were much more effective than regular splenocytes at inducing antigen-specific responses when used as APCs. This clearly demonstrates the feasibility of our approach to express exogenous proteins on the cell surface for therapeutic purposes.

This concept is tested in a lung carcinoma animal model. Two lung carcinoma lines of mouse origin, Lewis and Line 1 and the C58 tumor cells (rat lymphoma) will be used for the purpose of vaccination against tumors.

Chimeric proteins produced from nucleic acids comprising the nucleic acids of CSA fused to the nucleic acids of B7.1 (SEQ. ID No. 2), CD40L (SEQ. ID No. 6), or IL2 (SEQ. ID No. 4) will be used for display on the surface of these tumor cells and the cells will be used for vaccination of mice and rats against tumors. Briefly, tumor cells ($2\times10^7$) will be biotinylated as above. After several washes with PBS, the biotinylated cells will be incubated with chimeric proteins as above to bind the chimeric protein to the biotinylated cells. The chimera-decorated cells will be irradiated at 5–10,000 cGy and injected into tumor bearing animals to serve as a vaccine. Tumor regression is monitored. Based on the results as shown in the above examples, it is expected that this method will show up-regulation of the immune system.

It can be easily seen that other tumor systems and chimeric proteins can be identified, and the methods of this invention applied to provide other tumor vaccines and vaccines against infections.

This invention has been described in various preferred embodiments. Those skilled in the art will readily recognize that modifications, deviations or substitutions of the compounds or methods here disclosed may be made without departing from the spirit and scope of this invention. All such modifications, deviations and substitutions are considered to be within the scope of the claims of this invention.

What is claimed:

1. A protein encoded by a nucleic acid having the sequence of SEQ ID NO:2.

2. A nucleic acid having the sequence of SEQ ID NO:2.

3. An isolated cell comprising a protein encoded by a nucleic acid having the sequence of SEQ ID NO:2.

4. The isolated cell of claim 3, wherein the cell is selected from the group consisting of splenocytes, tumor cells, bone marrow cells, endothelial cells, and islet cells.

5. An isolated production cell comprising a nucleic acid having the sequence of SEQ ID NO:2.

6. A polypeptide product produced by the production cell of claim 5, wherein the polypeptide product is encoded by the nucleic acid having the sequence of SEQ ID NO:2.

7. An isolated target cell comprising a protein encoded by a nucleic acid having the sequence of SEQ ID NO:2, wherein the protein is displayed on the surface of the target cell.

8. The isolated target cell of claim 7, wherein the cell is selected from the group consisting of splenocytes, tumor cells, bone marrow cells, endothelial cells, and islet cells.

9. A tumor cell comprising a protein encoded by a nucleic acid having the sequence of SEQ ID NO:2, wherein the protein is displayed on the surface of the tumor cell.

10. A vaccine, wherein the vaccine comprises a number of tumor cells decorated with protein encoded by a nucleic acid having the sequence of SEQ ID NO:2 sufficient to generate a T-cell response when administered to a tumor-bearing animal.

11. A method of attaching an immune costimulatory agent to a tumor cell surface in vivo, the method comprising: contacting a biotinylated tumor cell with a chimeric protein comprising (i) the immune costimulatory agent and (ii) core streptavidin, wherein the immune costimulatory agent comprises the extracellular domain of B7.1, to form a tumor cell having a surface decorated with the chimeric protein.

12. The method of claim 11, wherein the tumor cell is a target cell.

13. The method of claim 11, wherein the chimeric protein is encoded by a nucleic acid having the sequence of SEQ ID NO:2.

14. The method of claim 11, wherein the method comprises administering the chimeric protein to a subject containing the biotinylated tumor cell.

15. The method of claim 11, further comprising the step of biotinylating a tumor cell to form the biotinylated tumor cell.

16. The method of claim 15, wherein the tumor cell is biotinylated at room temperature.

17. The method of claim 15, wherein the biotinylating step comprises contacting the tumor cell with a biotin-containing compound for a period lasting no more than about 30 minutes.

18. The method of claim 17, further comprising the step of washing the tumor cell to remove free biotin-containing compound.

19. The method of claim 17, wherein the biotin-containing compound comprises Sulfo-NHS-LC-biotin.

20. The method of claim 15, wherein the biotinylating is effected in vivo.

21. The method of claim 20, wherein the method comprises administering a biotin-containing compound to a subject containing the tumor cell.

22. The method of claim 21, wherein the biotin-containing compound comprises Sulfo-NHS-LC-biotin.

23. The method of claim 15, wherein the biotinylating is effected in vitro.

* * * * *

UNITED STATES PATENT AND TRADEMARK OFFICE
CERTIFICATE OF CORRECTION

PATENT NO. : 7,238,360 B2
APPLICATION NO. : 10/312245
DATED : July 3, 2007
INVENTOR(S) : Haval Shirwan It is certified that error appears in the above-identified patent and that said Letters Patent is hereby corrected as shown below:

Title page, item (73)
Assignee:

The assignee's name "Unversity of Louisville, Research Foundation, Inc." should read --University of Louisville, Research Foundation, Inc.--.

Signed and Sealed this

Sixteenth Day of September, 2008

JON W. DUDAS
*Director of the United States Patent and Trademark Office*